US009493656B2

(12) United States Patent
Lam et al.

(10) Patent No.: US 9,493,656 B2
(45) Date of Patent: Nov. 15, 2016

(54) PHENYL XANTHENE DYES

(71) Applicant: APPLIED BIOSYSTEMS, LLC, Carlsbad, CA (US)

(72) Inventors: Joe Y. L. Lam, Castro Valley, CA (US); Steven M. Menchen, Fremont, CA (US); Ruiming Zou, Foster City, CA (US); Scott C. Benson, Alameda, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/741,258

(22) Filed: Jun. 16, 2015

(65) Prior Publication Data
US 2015/0274975 A1 Oct. 1, 2015

Related U.S. Application Data

(60) Division of application No. 14/188,309, filed on Feb. 24, 2014, now Pat. No. 9,090,775, which is a continuation of application No. 13/742,667, filed on Jan. 16, 2013, now abandoned, which is a continuation of application No. 12/351,504, filed on Jan. 9, 2009, now Pat. No. 8,383,841, which is a continuation of application No. 10/837,621, filed on May 4, 2004, now Pat. No. 7,491,830.

(60) Provisional application No. 60/649,031, filed on May 9, 2003.

(51) Int. Cl.
C07D 311/82 (2006.01)
C09B 11/06 (2006.01)
C09B 11/12 (2006.01)
C09B 11/22 (2006.01)
C09B 11/24 (2006.01)
C09B 11/26 (2006.01)
C09B 13/00 (2006.01)
C07D 491/14 (2006.01)
C09B 57/00 (2006.01)
C09B 62/002 (2006.01)

(52) U.S. Cl.
CPC ............. C09B 11/24 (2013.01); C07D 311/82 (2013.01); C07D 491/14 (2013.01); C09B 11/06 (2013.01); C09B 11/12 (2013.01); C09B 11/22 (2013.01); C09B 11/26 (2013.01); C09B 13/00 (2013.01); C09B 57/00 (2013.01); C09B 62/0025 (2013.01)

(58) Field of Classification Search
CPC ..... C07D 311/82; C09B 11/06; C09B 11/12; C09B 11/22; C09B 11/24; C09B 11/26; C09B 13/00
See application file for complete search history.

(56) References Cited

U.S. PATENT DOCUMENTS

| 738,227 | A | | 9/1903 | Nastvogel |
| 1,532,790 | A | | 4/1925 | Weiler |
| 2,447,440 | A | | 8/1948 | Thurston et al. |
| 2,535,968 | A | | 12/1950 | Thurston et al. |
| 3,079,435 | A | | 2/1963 | Freifelder et al. |
| 4,318,846 | A | | 3/1982 | Khanna et al. |
| 4,329,461 | A | * | 5/1982 | Khanna ................. G01N 33/78 436/500 |
| 4,439,356 | A | * | 3/1984 | Khanna ................ C07D 311/82 435/188 |
| 4,445,904 | A | | 5/1984 | Hahnke et al. |
| 4,481,136 | A | | 11/1984 | Khanna et al. |
| 4,581,071 | A | | 4/1986 | Akutsu et al. |
| 4,640,893 | A | | 2/1987 | Mangel et al. |
| 4,983,498 | A | | 1/1991 | Rode et al. |
| 5,066,580 | A | | 11/1991 | Lee |
| 5,188,934 | A | | 2/1993 | Menchen et al. |
| 5,231,191 | A | | 7/1993 | Woo et al. |
| 5,366,860 | A | | 11/1994 | Bergot et al. |
| 5,389,489 | A | | 2/1995 | Yanagihara et al. |
| 5,410,053 | A | | 4/1995 | Hahn et al. |
| 5,442,045 | A | | 8/1995 | Haugland et al. |
| 5,654,419 | A | | 8/1997 | Mathies et al. |

(Continued)

FOREIGN PATENT DOCUMENTS

| AU | 5227898 | 6/1998 |
| CA | 2119840 | 9/1994 |

(Continued)

OTHER PUBLICATIONS

Derwent Abstract of JP 10-035108, Feb. 10, 1998.

(Continued)

Primary Examiner — Erich A Leeser

(57) ABSTRACT

Fluorescent phenyl xanthene dyes are described that comprise any fluorescein, rhodamine or rhodol comprising a particular C9 phenyl ring. One or both of the ortho groups on the lower C9 phenyl ring is ortho substituted with a group selected from alkyl, heteroalkyl, alkoxy, halo, haloalkyl, amino, mercapto, alkylthio, cyano, isocyano, cyanato, mercaptocyanato, nitroso, nitro, azido, sulfeno, sulfinyl, and sulfino. In one embodiment, halo and/or hydroxy groups are used. Optimal dyes contain a lower C9 phenyl ring in which both ortho groups are the same and the lower ring exhibits some form a symmetry relative to an imaginary axis running from the phenyl rings point of attachment to the remainder of the xanthene dye through a point para to the point of attachment. The phenyl xanthene dyes may be activated. Furthermore, the phenyl xanthene dyes may be conjugated to one or more substances including other dyes. The phenyl xanthene dyes are useful for a number of purposes, including labels for use in automated DNA sequencing as well the formation of fluorescent "bar codes" for polymeric particles used in the multiplexed analysis of analytes.

14 Claims, 5 Drawing Sheets

(56) References Cited

U.S. PATENT DOCUMENTS

Figure 1:
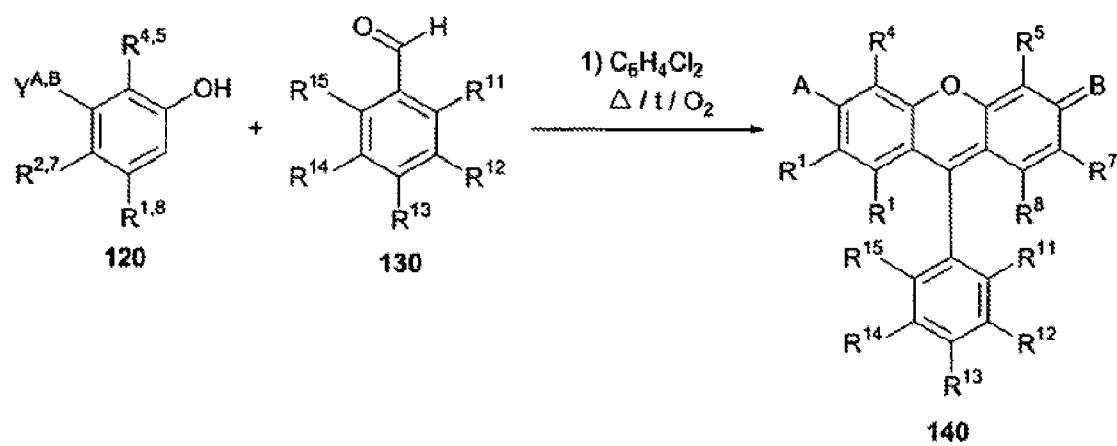

| | | | |
|---|---|---|---|
| 5,654,442 A | 8/1997 | Menchen et al. |
| 5,750,409 A | 5/1998 | Herrmann et al. |
| 5,800,996 A | 9/1998 | Lee et al. |
| 5,840,999 A | 11/1998 | Benson et al. |
| 5,847,162 A | 12/1998 | Lee et al. |
| 5,863,727 A | 1/1999 | Lee et al. |
| 5,936,087 A | 8/1999 | Benson et al. |
| 6,008,379 A | 12/1999 | Benson et al. |
| 6,020,481 A | 2/2000 | Benson et al. |
| 6,025,505 A | 2/2000 | Lee et al. |
| 6,123,921 A | 9/2000 | Meade et al. |
| 6,143,570 A | 11/2000 | Alder et al. |
| 6,191,278 B1 | 2/2001 | Lee et al. |
| 6,229,055 B1 | 5/2001 | Klaubert et al. |
| 6,248,884 B1 | 6/2001 | Lam et al. |
| 6,268,222 B1 | 7/2001 | Chandler et al. |
| 6,372,907 B1 | 4/2002 | Lee et al. |
| 6,399,392 B1 | 6/2002 | Haugland et al. |
| 6,552,199 B1 | 4/2003 | Daltrozzo et al. |
| 6,998,493 B2 | 2/2006 | Banning et al. |
| 7,432,298 B2 | 10/2008 | Lam et al. |
| 7,491,830 B2 | 2/2009 | Lam et al. |
| 7,550,570 B2 | 6/2009 | Lee et al. |
| 8,383,841 B2 | 2/2013 | Lam et al. |
| 2013/0171715 A1 | 7/2013 | Lam et al. |

FOREIGN PATENT DOCUMENTS

| | | | | |
|---|---|---|---|---|
| DE | 19926377 | | 12/2000 | |
| EP | 0623599 | | 9/1994 | |
| EP | 0892028 | A3 | 2/1999 | |
| EP | 0892028 | B1 | 2/2004 | |
| EP | 1394236 | | 3/2004 | |
| EP | 1422282 | | 5/2004 | |
| FR | 2300119 | | 9/1976 | |
| GB | 1454815 | | 2/1974 | |
| JP | 48-096625 | | 12/1973 | |
| JP | 51-103129 | | 9/1976 | |
| JP | 57-82387 | * | 10/1980 | ........... C07D 311/82 |
| JP | 60-25195 | | 2/1985 | |
| JP | 62-278570 | | 3/1987 | |
| JP | 02-127483 | | 5/1990 | |
| JP | 04-107559 | | 4/1992 | |
| JP | 10035108 | | 2/1998 | |
| JP | 11279426 | | 12/1999 | |
| JP | 2000-103975 | | 4/2000 | |
| JP | 2000-239272 | | 9/2000 | |
| WO | WO 97/39064 | * | 10/1997 | ............ C08B 11/00 |
| WO | WO-02/08245 | | 1/2002 | |
| WO | WO-02/074388 | | 9/2002 | |
| WO | WO-02/076397 | | 10/2002 | |
| WO | WO-2004/101709 | | 11/2004 | |

OTHER PUBLICATIONS

Machine Translation of JP 10-035108, Feb. 10, 1998.
Bukhteeva, et al., *Chemical Abstracts*, 108:48386, 1988.
Chen, Chii-Shiarng et al., "Redox-Dependent Trafficking of 2,3,4,5,6-Pentafluorodihydrotetramethylrosamine, A Novel Fluorogenic Indicator of Cellular Oxidative Activity", *Free Radical Biology & Medicine*, vol. 28, No. 8, 2000, 1266-1278.
Mohr, et al., "Application of Potential-sensitive fluorescent dyes in anion- and cation-sensitive polymer membranes", *Seniors and Actuators B., Elsevier Sequoia S.A.*, Lausanne, vol. 39 (1-3), Mar. 1, 1997, 239-245.
Panchuk-Voloshina, et al., "Alexa Dyes, a Series of New Fluorescent Dyes that Yield Exceptionally Bright, Photostable Conjugates", *J. Histochemistry & Cytochemistry*, vol. 47, No. 9, 1999, 1179-1188.
PCT/US2004/013798, PCT International Search Report from PCT/US2004/013798 dated Sep. 29, 2004.
PCT/US2004/013801, International Preliminary Report on Patentability issued Nov. 11, 2005.
PCT/US2004/013801, International Search Report and Written Opinion mailed Sep. 27, 2004.
Sulfinyl, retrieved from http://en.wikipedia.org/w/index.php?title=Sulfoxide&oldid=452204243 on Oct. 12, 2011.
Sulfonyl, retrieved from http://en.wikipedia.org/w/index.php?title=Sulfonyl&oldid=446418822 on Oct. 12, 2011.
Tsukanova, et al., "Microscopic organization of long-chain rhodamine molecules in monolayers at the air/water intersurface", *Journal of Physical Chemistry*, vol. 106, No. 16, 2002, 4203-4213.

* cited by examiner

PHENYL XANTHENE DYES

1. CROSS-REFERENCE TO RELATED APPLICATIONS

This application is a divisional of U.S. application Ser. No. 14/188,309 filed Feb. 24, 2014, which is a continuation of U.S. application Ser. No. 13/742,667 filed Jan. 16, 2013, now abandoned, which is a continuation of U.S. application Ser. No. 12/351,504 filed Jan. 9, 2009, now U.S. Pat. No. 8,383,841, which is a continuation of U.S. application Ser. No. 10/837,621 filed May 4, 2004, now U.S. Pat. No. 7,491,830, and claims benefit of priority to U.S. provisional patent application No. 60/469,031 filed May 9, 2003 entitled "Phenyl Xanthene Dyes," the entire disclosure of which is incorporated herein by reference.

2. BACKGROUND OF THE INVENTION

2.1. Field of the Invention

Fluorescent phenyl xanthene dyes are described herein. More specifically, fluorescent phenyl rhodamines, phenyl fluoresceins and phenyl rhodols are described herein

2.2 Description of Related Art

Dyes, including various fluorescein, rhodamine and rhodol dyes, are known. However, there is an ever present need to develop improved fluorescent dyes, especially dyes that exhibit enhanced fluorescence and enhanced stability. In addition, there is a need to develop dyes that can be employed, if desired, in polymeric beads or particles. These and other needs are met by the various dyes described herein.

3. SUMMARY OF THE INVENTION

Phenyl xanthene dyes are described herein that exhibit useful fluorescent properties. The phenyl xanthene dyes comprise any fluorescein, rhodol or rhodamine ring system where the phenyl substituent at the 9-carbon ("the C9 phenyl ring") is a specific type of phenyl ring. For the purposes of this description, fluoresceins, rhodols and rhodamines are numbered in the following manner:

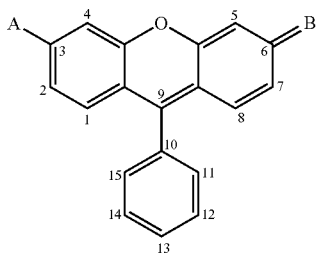

where A is either a hydroxyl or an amine group and B is a either an oxo or an imminium group. The C9 phenyl ring on the phenyl xanthene dye, whether substituted or unsubstituted, may be referred to as the "lower ring." The remainder of the molecule may be referred to as the "upper ring system."

The C9 phenyl ring is substituted at one or both of carbons C11 or C15 with a group selected from alkyl, heteroalkyl, alkoxy, halo, haloalkyl, amino, alkylthio, cyano, isocyano, cyanato, mercaptocyanato, nitro, and sulfinyl. When both the C11 and C15 carbons are substituted, the substitutents may be the same or different. Thus, in one embodiment, the phenyl xanthene dyes comprise any fluorescein, rhodol, or rhodamine that comprises a C9 phenyl ring comprising the following structure:

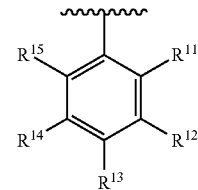

where at least one of $R^{11}$ or $R^{15}$ is selected from alkyl, heteroalkyl, alkoxy, halo, haloalkyl, amino, alkylthio, cyano, isocyano, cyanato, mercaptocyanato, nitro, and sulfinyl.

The remaining carbons on the C9 phenyl ring can, independently of one another, be unsubstituted or substituted with any group having no more than 40 atoms and typically no more than 25 atoms. Illustrative substituent groups that can be positioned at carbons C12, C13 and/or C14 include alkyl, heteroalkyl, aryl, heteroaryl, alkoxy, halo, haloalkyl, amino, alkylthio, cyano, isocyano, cyanato, mercaptocyanato, nitro, sulfinyl, sulfonyl, sulfonamide, carboxyl, and carboxyamide. Accordingly, in another embodiment, at least one of $R^{11}$ or $R^{15}$ is substituted as described above and the remainder of $R^{11}$, $R^{12}$, $R^{13}$, $R^{14}$ and $R^{15}$ are, independently of one another, selected from hydrogen, alkyl, heteroalkyl, aryl, heteroaryl, alkoxy, halo, haloalkyl, amino, alkylthio, cyano, isocyano, cyanato, mercaptocyanato, nitro, sulfinyl, sulfonyl, sulfonamide, carboxyl, and carboxyamide.

It has been discovered that phenyl xanthene dyes, including a C9 phenyl that is substituted with halo, haloalkyl, alkoxy and/or nitrile substituents, exhibit especially good fluorescent properties particularly when placed at the C11 and/or C15 carbons. Accordingly, in another embodiment, at least one of $R^{11}$ and $R^{15}$ is selected from an alkoxy, halo, haloalkyl and/or nitrile. In yet another embodiment, $R^{11}$ and $R^{15}$ are each, independently of one another, an alkoxy, halo, haloalkyl and/or nitrile.

In still another embodiment, at least one of $R^{11}$ and $R^{15}$ is selected from an alkoxy, halo and/or haloalkyl and the remainder of $R^{11}$, $R^{12}$, $R^{13}$, $R^{14}$ and $R^{15}$ are, independently of one another, selected from hydrogen, alkoxy, halo and/or haloalkyl. In another embodiment, $R^{11}$ and $R^{15}$ are each, independently of one another, an alkoxy, halo and/or haloalkyl and the remainder of $R^{12}$, $R^{13}$ and $R^{14}$ are, independently of one another, selected from hydrogen, alkoxy, halo and/or haloalkyl. Any alkoxy and/or halo and/or haloalkyl groups present on the lower phenyl ring may be the same or different. However, in one embodiment, any alkoxy and/or halo and/or haloalkyl groups present on the lower phenyl ring is identical to any other alkoxy and/or halo and/or haloalkyl groups present on the phenyl ring. Furthermore, in one embodiment, the lower phenyl ring is only substituted with hydrogen, alkoxy, halo and/or haloalkyl groups.

Especially suitable alkoxy groups include (C1 to C20) oxyalkyls, particularly methoxy. In one embodiment, the phenyl ring is only substituted with hydrogen and identical alkoxy groups. In one embodiment at least two groups on the phenyl ring are alkoxy. In another embodiment at least three groups on the phenyl ring are alkoxy. In another embodiment at least four groups on the phenyl ring are alkoxy. In another embodiment all of the groups on the phenyl ring are alkoxy.

Especially suitable halos include chloro and fluoro groups. In one embodiment, the phenyl ring is only substituted with hydrogen and identical halo groups, such as fluoro or chloro. In one embodiment at least two groups on the phenyl ring are halo. In another embodiment at least three groups on the phenyl ring are halo. In another embodiment at least four groups on the phenyl ring are halo. In another embodiment all of the groups on the phenyl ring are halo.

Especially suitable haloalkyls include —CF3. Accordingly, in one embodiment, the phenyl ring is only substituted with hydrogen and haloalkyl groups such as —CF3 groups. In one embodiment at least two groups on the phenyl ring are haloalkyl. In another embodiment at least three groups on the phenyl ring are haloalkyl. In another embodiment at least four groups on the phenyl ring are haloalkyl. In a another embodiment all of the groups on the phenyl ring are haloalkyl.

Embodiments where the C9 phenyl ring is substituted at both the C11 and C15 carbons also exhibit especially good fluorescent properties. Accordingly, in one embodiment, $R^{11}$ and $R^{15}$ are each, independently of one another, selected from alkyl, heteroalkyl, alkoxy, halo, haloalkyl, amino, alkylthio, cyano, isocyano, cyanato, mercaptocyanato, nitro, and sulfinyl. The remaining carbons on the phenyl need not be substituted and, if substituted, the substituents may, independently, be the same or different when compared to $R^{11}$ and/or $R^{15}$.

Embodiments where the C9 phenyl ring is identically substituted at both carbons ortho to the point of the phenyl ring's attachment to the remainder of the phenyl xanthene dye also exhibit desirable fluorescent properties. Accordingly, in another embodiment, $R^{11}$ and $R^{15}$ are identical. Once again, the remaining carbons on the phenyl need not be substituted and, if substituted, the substituents may, independently, be the same or different when compared to $R^{11}$ and $R^{15}$. In one embodiment, any substituents on the lower phenyl ring are identical.

Symmetry appears to be an important factor in selecting optimal C9 phenyl rings. In this regard, the symmetry is relative to an imaginary axis running from the lower phenyl ring's point of attachment to the remainder of the phenyl xanthene dye (i.e., the 10-carbon) through a point para to the attachment (i.e., the 13-carbon). Accordingly, in one embodiment, $R^{11}$ and $R^{15}$ are identical and the remainder of $R^{12}$, $R^{13}$ and $R^{14}$ are, identically, either hydrogen or a substituent different from $R^{11}$ and $R^{15}$. In another embodiment $R^{11}$, $R^{13}$, and $R^{15}$ are identical and the remainder of $R^{12}$, $R^{13}$, and $R^{14}$ are, identically, either hydrogen or a substituent different from $R^{11}$, $R^{13}$ and $R^{15}$. In yet another embodiment, $R^{11}$, $R^{12}$, $R^{14}$ and $R^{15}$ are identical and $R^{13}$ is either hydrogen or a substituent different from $R^{11}$, $R^{12}$, $R^{14}$ and $R^{15}$. In still another embodiment, $R^{11}$, $R^{12}$, $R^{13}$, $R^{14}$ and $R^{15}$ are all identical. Optimal lower phenyl rings include those where the ring exhibits one of the aforementioned symmetries and $R^{11}$ and $R^{15}$ are selected from the same, alkoxy and/or halo and/or haloalkyl groups.

The C9 phenyl ring departs from known C9 phenyl rings in phenyl xanthene dyes in many ways. For example, as evident from the patent literature, it is conventional wisdom to substitute the ortho phenyl position with a carboxyl or sulfonyl group, or some derivative thereof, such as an ester, amide, acid halide or salt. See, e.g., U.S. Pat. No. 6,248,884, U.S. Pat. No. 6,229,055, U.S. Pat. No. 5,936,087, U.S. Pat. No. 5,847,162, U.S. Pat. No. 5,840,999, U.S. Pat. No. 5,750,409, U.S. Pat. No. 5,654,442, U.S. Pat. No. 5,442,045, U.S. Pat. No. 5,410,053, U.S. Pat. No. 5,366,860, U.S. Pat. No. 5,231,191, U.S. Pat. No. 5,188,934, U.S. Pat. No. 5,066,580, U.S. Pat. No. 4,481,136 and U.S. Pat. No. 4,439,356. However, the instant C9 phenyl rings do not contain the aforementioned ortho carboxyl, ortho sulfonyl, or an ester, amide, acid halide, or salt thereof.

The C9 phenyl ring can be connected to any fluorescein, rhodol or rhodamine type upper ring system. Rhodamines are phenyl xanthenes that additionally comprise an exocyclic amine group and an exocyclic imminium group. Rhodols are phenyl xanthenes that additionally comprise an exocyclic amine group and an exocyclic oxo group. Fluoresceins are phenyl xanthenes that additionally comprise an exocyclic hydroxyl group and an exocyclic oxo group. The phenyl xanthene dyes described can employ any fluorescein, rhodol and rhodamine type upper ring system as long as the C9 phenyl attached thereto is as described herein. Accordingly, in one embodiment, the phenyl xanthene dye comprises a fluorescein type upper ring system. In another embodiment, the phenyl xanthene dye comprises a rhodol type upper ring system. In another embodiment, the phenyl xanthene dye comprises a rhodamine type upper ring system.

Suitable fluorescein, rhodamine and rhodol type upper ring systems are provided, for example, in U.S. Pat. No. 6,248,884, U.S. Pat. No. 6,229,055, U.S. Pat. No. 5,936,087, U.S. Pat. No. 5,847,162, U.S. Pat. No. 5,840,999, U.S. Pat. No. 5,750,409, U.S. Pat. No. 5,654,442, U.S. Pat. No. 5,442,045, U.S. Pat. No. 5,410,053, U.S. Pat. No. 5,366,860, U.S. Pat. No. 5,231,191, U.S. Pat. No. 5,188,934, U.S. Pat. No. 5,066,580, U.S. Pat. No. 4,481,136 and U.S. Pat. No. 4,439,356, all of which relate to phenyl xanthenes and all of which are hereby incorporated by reference. However, the upper ring system is not limited to the structures described in these patents. As stated, any fluorescein, rhodol or rhodamine type upper ring system can be employed as long as it is attached to the C9 phenyl ring described herein.

Furthermore, as known in the art, phenyl xanthene dyes can be extended to include a 3,4- and/or a 5,6-benzo substituent (see, e.g., U.S. Pat. No. 6,248,884, U.S. Pat. No. 5,750,409 and U.S. Pat. No. 5,066,580). In "extended" fluoresceins, rhodols and rhodamines, the exocyclic amine or hydroxyl group and/or the exocyclic imminium or oxo group are attached to any present 3,4- and/or 5,6-benzo substituents. These "extended" fluorescein, rhodol and rhodamine rings can also be employed in the invention as long as they comprise the C9 phenyl described herein. Accordingly, the "fluorescein," "rhodol" and "rhodamine" as used herein embrace extended structures.

In one embodiment, the phenyl xanthene dyes not only contain the new lower phenyl ring but also contain sufficient lipophilic groups to make the phenyl xanthenes lipid soluble. This is especially beneficial when the phenyl xanthenes are used, for example, to imbibe hydrophobic, polymeric particles that are useful in aqueous assays. Non-limiting examples of such polymeric particles include crosslinked and uncrosslinked polystyrene particles and styrene-(meth) acrylic acid copolymers. As evident to one of ordinary skill in the art, an unlimited variety of particles for use in assays are commercially available, including particles that are functionalized and/or paramagnetic and/or conjugated with one or more biological reagents. In such embodiments, the degree of lipid solubility required for the phenyl xanthene dye necessarily varies as a function of the polymer) utilized, the aqueous solvent or solvent system employed in the assay in which the polymeric particle is to be used, and the conditions (e.g., time, temperature, pressure, pH, etc.) under which the assay is run. Suitable degrees of lipid solubility are easily determined by methods known in the art. For example, suitable lipid solubility can be determined by a partition test wherein a known quantity of dye in organic solvent is combined with the aqueous solvent or solvent system used in the assay. If a partition results and, under the conditions used in the assay, there is no appreciable crossing by the dye into the solvent or solvent system, then the dye is sufficiently lipid soluble. Put another way, the lipid soluble phenyl xanthene dye should be sufficiently lipid soluble such that it is capable of being imbibed into the polymer when dissolved in an organic solvent or solvent system and, when the dyed polymer is subjected to the aqueous conditions of the assay, the dye should resist leaching out of the polymer to any degree that significantly impacts the fluorescent signature of the dye imbibed polymer or the results of the assay.

In those embodiments where the phenyl xanthene dyes are lipid soluble rhodamines, one or both of the exocyclic amine and exocyclic imminium nitrogens are often substituted with one or more lipophilic groups designed to impart to the rhodamine lipophilic characteristics or properties. Thus, useful dyes include rhodamines that comprise the lower phenyl ring described above and also comprise one or two lipophilic substituents at the exocyclic amine nitrogen and/or one or two lipophilic substituents at the exocyclic imminium nitrogen. In one embodiment, both the exocyclic amine nitrogen and the exocyclic imminium nitrogen are substituted with a lipophilic group. In another embodiment, the exocyclic amine nitrogen and the exocyclic imminium nitrogen are both substituted with two lipophilic groups. The lipophilic groups, whether attached to the same or different exocyclic nitrogen, may be the same or different. In one embodiment, the lipophilic groups on the exocyclic nitrogens are the same. In those embodiments where the phenyl xanthene dyes are lipid soluble rhodols, the exocyclic amine nitrogen is often substituted with one or more lipophilic groups designed to impart to the rhodol lipophilic characteristics or properties. Thus, useful dyes include rhodols that comprise the C9 phenyl described herein and also comprise one or two lipophilic substituents at the exocyclic amine nitrogen. In one embodiment, the exocyclic amine nitrogen is substituted with one lipophilic group. In another embodiment, the exocyclic amine nitrogen is substituted with two lipophilic groups. If there are two lipophilic groups on the exocyclic amine nitrogen, the lipophilic groups may be same or different. In one embodiment, there are two lipophilic groups on the exocyclic amine nitrogen that are the same.

Lipid-soluble phenyl xanthene dyes may include lipophilic substituents at other positions as well. It is the net effect of the lipophilic' substituents that determines whether the phenyl xanthene dye is lipid soluble. This is especially true for fluoresceins which have no exocyclic amine or imminium nitrogens.

Lipophilic substituents are groups that impart the resultant phenyl xanthene dye with lipophilic characteristics or properties as denoted above. The nature of each lipophilic substituent is not critical, as long as the resultant phenyl xanthene dye is lipid soluble. Non-limiting examples of suitable lipophilic substituents include unsubstituted (C4-C20) alkyls, (C5-C40) aryls, and (C6-C40) arylalkyls. Depending on the number of methylene and methine units in the lipophilic substituent, the lipophilic substituent may also include pendant or internal polar or hydrophilic groups. For example, a lipophilic substituent may include one or more internal heteroatoms, such as one or more internal O, S, N or NH groups. As another example, a lipophilic substituent may include one or more pendant polar or hydrophilic substituents, such as one or more pendant halogen, —OH, —SH, —NH$_2$, —C(O)OH, —C(O)NH$_2$ or other polar or hydrophilic groups. Thus, lipophilic substituents may also include substituted (C4-C20) alkyl, substituted (C5-C40) aryls and substituted (C6-C40) arylalkyls, as well as substituted and unsubstituted (C4-C20) heteroalkyl, substituted and unsubstituted (C5-C40) heteroaryls and substituted and unsubstituted (C6-C40) arylalkyls. The number of internal or pendant polar or hydrophilic groups that may be included in a lipophilic substituent will depend upon, among other factors, the number of methylene or methine groups included in the lipophilic substituent and the number of lipophilic substituents on the phenyl xanthene dye. The nature and number of lipophilic groups necessary to make a phenyl xanthene lipid soluble can vary from molecule to molecule, and will be apparent to those of skill in the art.

Oftentimes, it is desirable to attach fluorescent dyes such as the phenyl xanthene dyes described herein to substances such as solid supports, particles, and biological and non-biological molecules (e.g., drugs, amino acids, peptides, polypeptides, proteins, nucleosides, nucleotides, oligonucleotides, polynucleotides, carbohydrates, etc.) Thus, in one embodiment, the various phenyl xanthene dyes described herein include one or more moieties suitable for such attachment. Such moieties are expressed by the formula —S-LG where S is a direct bond or a spacing moiety and LG is a linking group capable of forming a linkage with the substance to be conjugated. The linking group LG may be any moiety capable of forming the linkage, which may be covalent or non-covalent. For example, the linking group may be one member of a pair of specific binding molecules that non-covalently bind one another, such as biotin and avidinstreptavidin. Thus, in one embodiment, the linking group is biotin. Alternatively, the linking group may be a functional group capable of forming a covalent linkage with a "complementary" functional group, such as an electrophilic (or nucleophilic) group which is capable of forming a covalent linkage with a complementary nucleophilic (or electrophilic) group, although other groups may be used depending on the desired linking chemistry, as is well known in the art. The linking group may be attached directly to the phenyl xanthene dye or it may be spaced away from the phenyl xanthene dye by way of spacing moiety "S." As will be appreciated by skilled artisans, the nature and composition of the spacing moiety is not critical and may depend upon the particular application. The linking group, whether attached directly or spaced away via spacing moiety "S," may be attached to any available position of the phenyl xanthene dye. For example, the linking group may be attached to any available position on the upper ring system or the lower ring. In one embodiment, the linking group —S-LG is attached to the C2, C4, C5, or C7 position of the upper ring system. In another embodiment, the linking group —S-LG is attached to the C12, C13 or C14 position of the lower ring.

Alternatively, the lipid-soluble phenyl xanthene dyes may be linked to a conjugated substance. In this embodiment, at least one substituent on the phenyl xanthene dye is —S$^1$-LK-S$^2$—CS, where S$^1$ and S$^2$ are, independently of one another, a direct bond or a spacing moiety, LK represents a linkage, which may be a bond or another type of linkage, and CS is a conjugated substance. Non-limiting examples of substances that can be conjugated include glass substrates, metal substrates, polymeric substrates, biomolecules, haptens, drugs, poisons, vitamins, antigens, and pathogens. Once again, the linker will vary depending the identity of the conjugated substance.

Similarly, the phenyl xanthene dye may be part of an energy transfer ("ET") network comprising, for example, from two to four dyes covalently attached to one another that transfer energy to generate a longer Stoke's shift. In other words, the phenyl xanthene dye may be part of series of dyes that are covalently attached to one another. One example of an ET network would be a fluorescence resonance energy transfer ("FRET") dye. In this embodiment, at least one substituent on the phenyl xanthene dye is $-S^1$-LK-$S^2$-D, where $S^1$ and $S^2$ are, independently of one another, a direct bond or a spacing moiety, LK represents a linkage, which may be a bond or another type of linkage, and D is a dye. Linkages for covalently attaching phenyl xanthene dyes to other dyes are known in the art, as are suitable locations for attachment to the phenyl xanthene dyes (see, e.g., U.S. Pat. Nos. 5,800,996 and 5,863,727). In one embodiment, each dye in the energy transfer network is within 5 to 100 Å of the neighboring dye or dyes in the network to which it is covalently attached. In such embodiments, the phenyl xanthene dye can be the donor, acceptor, or an intermediate dye in the network.

In a more particular embodiment, the phenyl xanthene dyes are any fluorescent dye that comprises one of the following "core structures:"

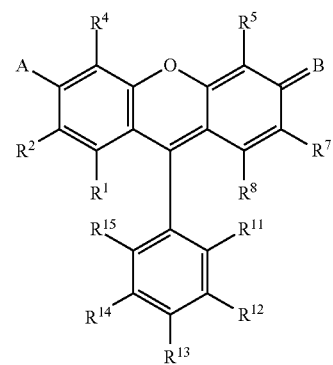

(I)

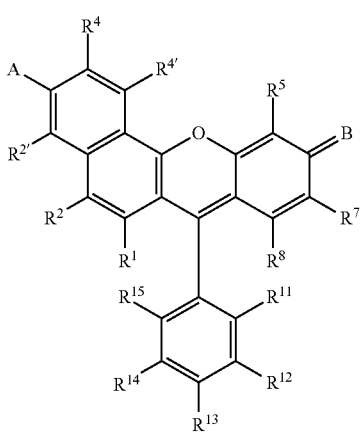

(II)

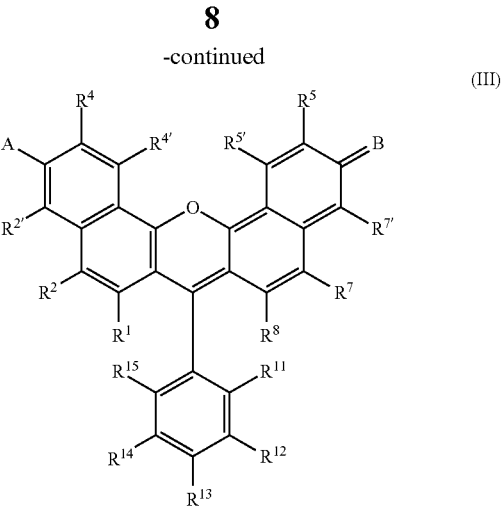

(III)

where A is —OH or $NR^{3'}R^{3''}$, where B is a =O or =$N^{\oplus}R^{6'}R^{6''}$ where $R^{11}$ and $R^{15}$ are, independently of one another, selected from alkyl, heteroalkyl, alkoxy, halo, haloalkyl, amino, alkylthio, cyano, isocyano, cyanato, mercaptocyanato, nitro, and sulfinyl, and the remainder of $R^1$, $R^2$, $R^{2'}$, $R^{3'}$, $R^{3''}$, $R^4$, $R^{4'}$, $R^5$, $R^{5'}$, $R^{6'}$, $R^{6''}$, $R^7$, $R^{7'}$, $R^8$, $R^{12}$, $R^{13}$, and $R^{14}$ are, independently of one another, selected from hydrogen and a substituent having no more than 40 atoms, and typically no more than 25 atoms. In one embodiment, the phenyl xanthene dye is lipid soluble. In another embodiment, one or more of the remainder of $R^1$, $R^2$, $R^{2'}$, $R^{3'}$, $R^{3''}$, $R^4$, $R^{4'}$, $R^5$, $R^{5'}$, $R^{6'}$, $R^{6''}$, $R^7$, $R^{7'}$, $R^8$, $R^{12}$, $R^{13}$, and $R^{14}$ may be —S-LG where S is a direct bond or a spacing moiety and LG is a linking group. In another embodiment one or more of the remainder of $R^1$, $R^2$, $R^{2'}$, $R^{3'}$, $R^{3''}$, $R^4$, $R^{4'}$, $R^5$, $R^{5'}$, $R^{6'}$, $R^{6''}$, $R^7$, $R^{7'}$, $R^8$, $R^{12}$, $R^{13}$, and $R^{14}$ may be $-S^1$-LK-$S^2$—CS, where $S^1$ and $S^2$ are each, independently of one another, a direct bond or a spacing moiety, LK is a linkage, and CS is a conjugated substance.

The phenyl xanthene dyes are useful in any commonly known application for dyes. For example the dyes are useful as fluorescent labels for automated DNA sequencing, oligonucleotide hybridization methods, detection of polymerase-chain reaction products, immunoassays, and the like. In addition, the dyes may be imbibed into polymeric particles for use in the standardization of fluorescence-based instrumentation, as a biological tracer, and in the detection and analysis of biomolecules. In these latter applications, it is often desirable for the dyes to be lipid soluble as previously discussed.

4. BRIEF DESCRIPTION OF THE DRAWINGS

Figure 2A:
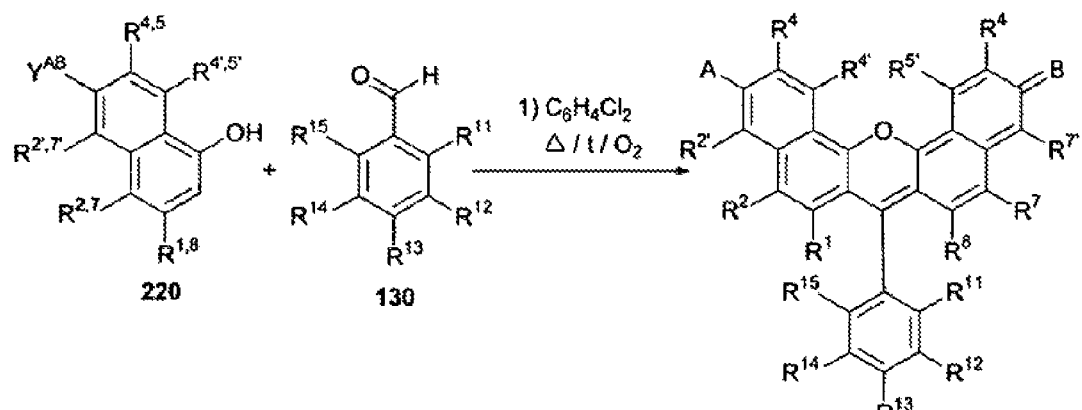
Figure 2B:
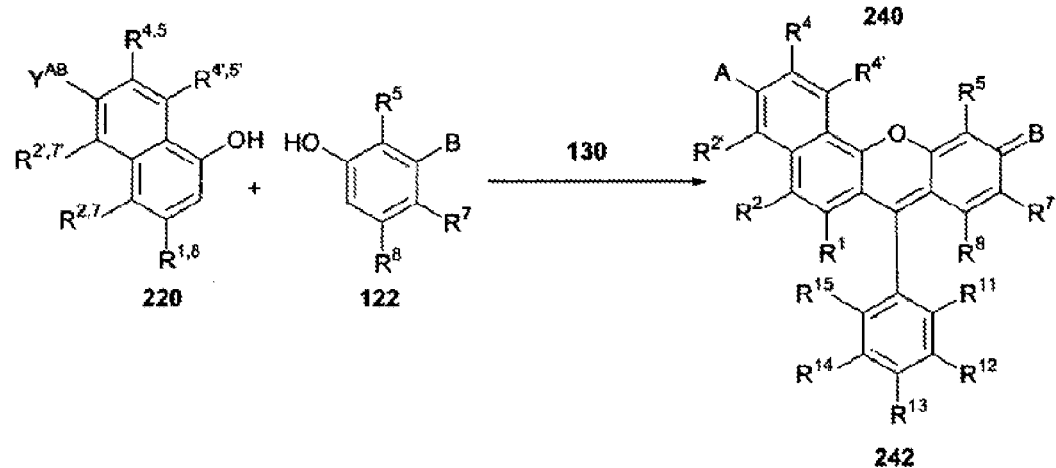
Figure 3:
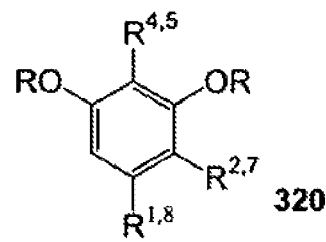
Figure 3:
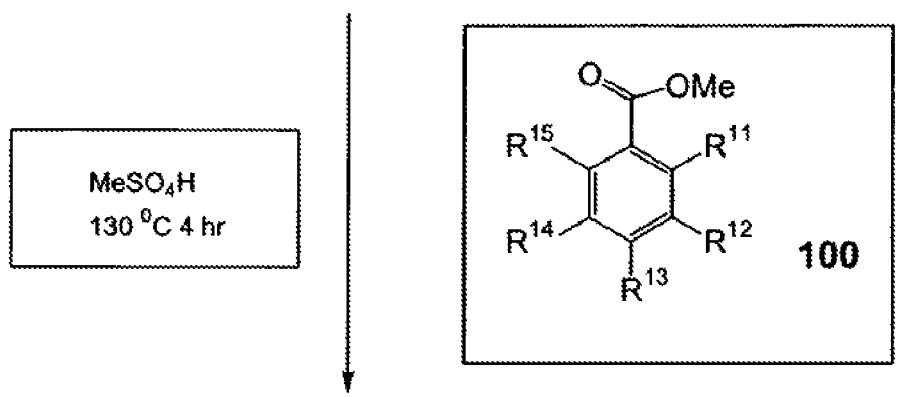
Figure 3:
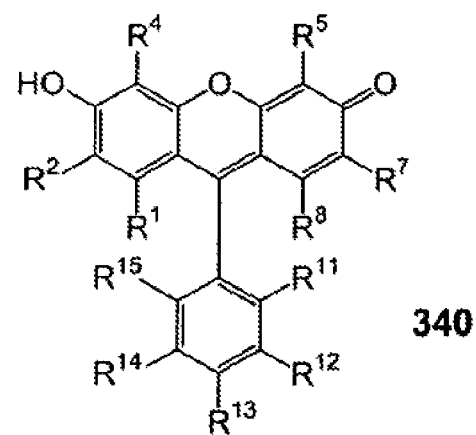
Figure 4:
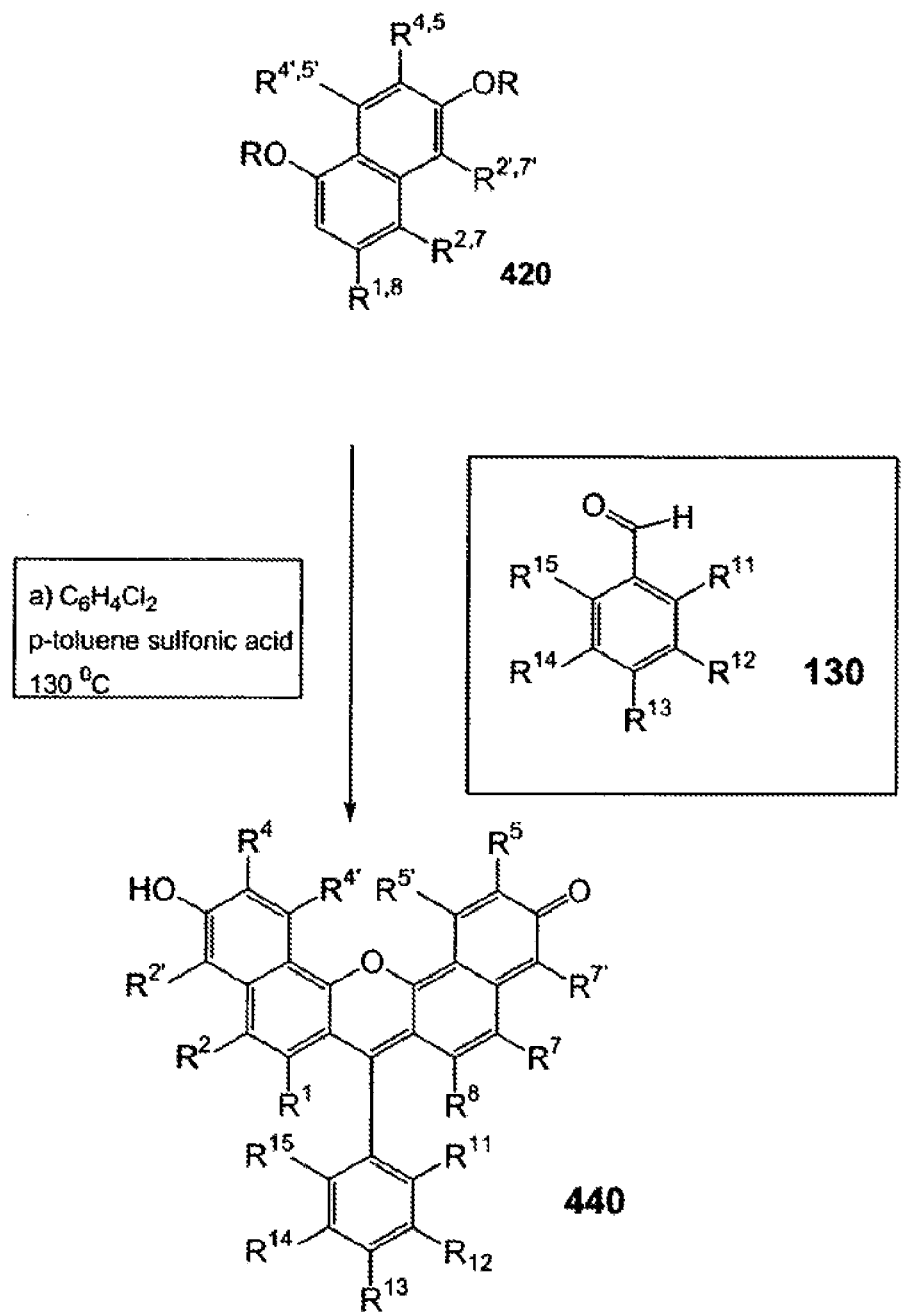
Figure 5:
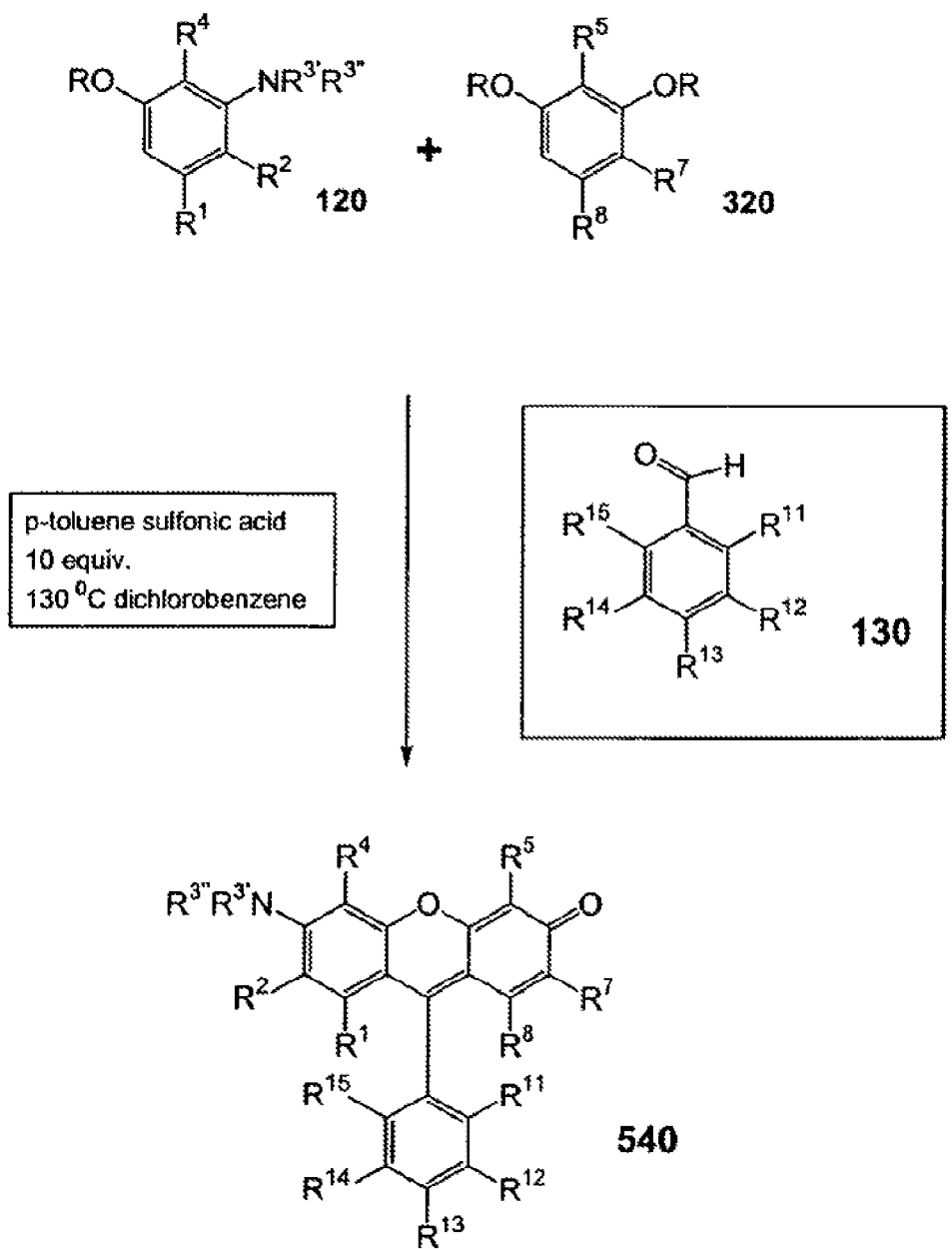

FIG. 1 illustrates the synthesis of phenyl xanthene dyes;
FIGS. 2A and 2B illustrate the synthesis of extended phenyl xanthene dyes;
FIG. 3 illustrates the synthesis of fluoresceins;
FIG. 4 illustrates the synthesis of extended fluoresceins; and
FIG. 5 illustrates the synthesis of a rhodol.

5. DETAILED DESCRIPTION OF THE PREFERRED EMBODIMENTS

5.1 Numbering System

For the purposes of the present application, carbon atoms in phenyl xanthenes such as fluoresceins, rhodols and rhodamines, or extended versions thereof, are numbered in the following manner:

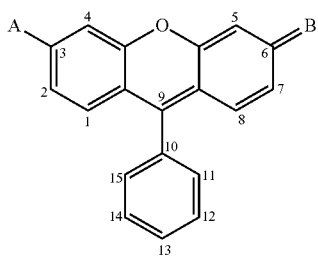

(Formula 1)

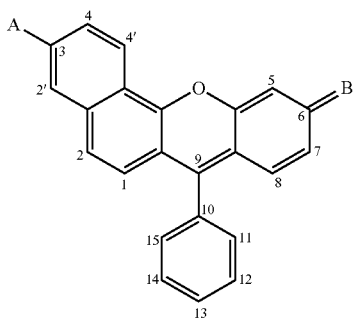

(Formula 2)

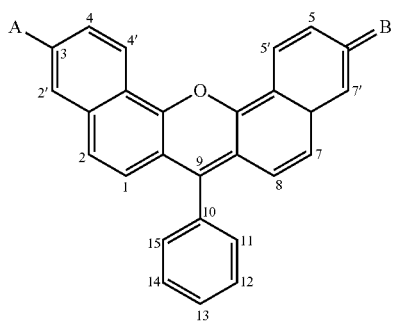

(Formula 3)

where A is either a hydroxyl (—OH) or an amine (—NH$_2$) and B is either an oxo (═O) or an imminium (═NH$_2^{\oplus}$).

5.2 Definitions

As used herein, the following terms are intended to have the following meanings:

"Phenyl Xanthene Dye," as used herein, refers to any dye that comprises a xanthene ring or an extended xanthene ring that is substituted with a C9 phenyl group, an exocyclic amine or hydroxyl group and an excyclic imminium or oxo group, as shown in formulae (1), (2) and (3) above. As known in the art, various substitutions may be made for the hydrogens on any of the 1-, 2-, 2'-, 4-, 4'-, 5'-, 5-, 7'-, 7-, 8-, 11-, 12-, 13-, 14-, and 15-carbons, as well as any hydrogens on any exocyclic amine or exocyclic imminium present. Substitutions can be independently selected from any of a wide variety of the same or different groups known in the art including, but not limited to, —X, —R$^S$, —OR$^S$, —SR$^S$, —NR$^S$R$^S$, perhalo, (C1-20) alkyl, —CX$_3$, —CN, —OCN, —SCN, —NCO, —NCS, —NO, —NO$_2$, —N$_3$, —S(O)$_2$O$^-$, —S(O)$_2$OH, —S(O)$_2$R$^S$, —C(O)R$^S$, —C(O)X, —C(S)R$^S$, —C(S)X, —C(O)OR$^S$, —C(O)OR$^S$, —C(O)OR$^S$, —C(S)SR$^S$, —C(O)NR$^S$R$^S$, —C(S)NR$^S$R$^S$ and —C(NR$^S$)NR$^S$R$^S$, where each X is independently a halogen (e.g., fluoride or chloride), and each R$^S$ is independently hydrogen, (C1-C20) alkyl or heteroalkyl, (C5-C20) aryl or heteroaryl, and (C6-C40) arylalkyl or heteroarylalkyl. Any of the aforementioned substituents can, in turn, be further substituted with one or more of the same or different substituents.

Moreover, the 1- and 2-substituents or the 2- and 2'-substituents, and/or the 7' and 7 substituents or the 7- and 8-substituents, can be taken together to form substituted or unsubstituted (C5-C20) benzo, naptho or polycyclic aryleno bridges. The bridges may, in turn, be further substituted, for example, with any of the substituents R$^S$ above.

When A is an amine and/or B is an imminium, the exocyclic nitrogen or nitrogens can be included in 5 or 6 membered rings involving the nitrogen atom and an adjacent carbon atom on the xanthene dye. The rings may, in turn, be further substituted, for example, with any of the substituents R$^S$ above.

"Rhodamine," as used herein, is a specific type of phenyl xanthene dye. Rhodamines embrace any substituted or unsubstituted dye that comprises one of formulae (1), (2) and (3) above, where A is a substituted or unsubstituted amine group and B is a substituted or unsubstituted imminium group. Examples of the various substitutions that may be made for hydrogens at the 1-, 2-, 2'-, 4-, 4'-, 5'-, 5-, 7'-, 7-, and 8-carbons, as well as hydrogens at the amine and imminium nitrogens are illustrated, for example, in U.S. Pat. No. 6,372,907, U.S. Pat. No. 6,248,884, U.S. Pat. No. 5,936,087, U.S. Pat. No. 5,847,162, U.S. Pat. No. 5,840,999, U.S. Pat. No. 5,750,409, U.S. Pat. No. 5,410,053, U.S. Pat. No. 5,366,860, and U.S. Pat. No. 5,231,191.

"Rhodol," as used herein, is another specific type of phenyl xanthene dye. Rhodols embrace any substituted or unsubstituted dye that comprises one of formulae (1), (2) and (3) above, where A is a substituted or unsubstituted amine group and B is an oxo group. Examples of the various substitutions that may be made for hydrogens at the 1-, 2-, 2'-, 4-, 4'-, 5'-, 5-, 7'-, 7-, and 8-carbons, as well as hydrogens at the amine nitrogen are illustrated, for example, in U.S. Pat. No. 6,372,907, U.S. Pat. No. 6,229,055, U.S. Pat. No. 6,008,379, U.S. Pat. No. 5,840,999, and U.S. Pat. No. 5,442,045.

"Fluorescein," as used herein, is another specific type of phenyl xanthene dye. Fluoresceins embrace any substituted or unsubstituted dye that comprises one of formulae (1), (2) and (3) above, where A is a hydroxyl group and B is an oxo group. Examples of the various substitutions that may be made for hydrogens at the 1-, 2-, 2'-, 4-, 4'-, 5'-, 5-, 7'-, 7-, and 8-carbons are illustrated, for example, in U.S. Pat. No. 6,229,055, U.S. Pat. No. 5,840,999, U.S. Pat. No. 5,654,442, U.S. Pat. No. 5,750,409, U.S. Pat. No. 5,188,934, U.S. Pat. No. 5,066,580, U.S. Pat. No. 4,481,136, and U.S. Pat. No. 4,439,356.

"Fluorescent Dye" or "Fluorescer" or "Fluorochrome" or "Fluorophore" as used interchangeably herein refer to molecules that absorb electromagnetic radiation at one wavelength and emit electromagnetic radiation at another wavelength in passing from a higher to a lower electronic state.

"Carboxyl" as used herein, is defined to include not only the carboxyl group (—COOH or —CO$_2$H) but also carboxylate radicals (—CO$_2^-$).

"Sulfonyl," as used herein, is defined to include not only the sulfonyl group (—SO$_2$OH or —SO$_3$H), but also sulfonate radicals (—SO$_3^-$).

"Biomolecule" as used herein refers to a molecule of a type typically found in a biological system, whether such molecule is naturally occurring or the result of some external disturbance of the system (e.g., a disease, poisoning, genetic manipulation, etc.), as well as synthetic analogs and derivatives thereof. Non-limiting examples of biomolecules include amino acids (naturally occurring or synthetic), peptides, polypeptides, glycosylated and unglycosylated proteins (e.g., polyclonal and monoclonal antibodies, receptors, interferons, enzymes, etc.), nucleosides, nucleotides, oligonucleotides (e.g., DNA, RNA, PNA oligos), polynucleotides (e.g., DNA, cDNA, RNA, etc.), carbohydrates, hormones, haptens, steroids, toxins, etc. Biomolecules may be isolated from natural sources, or they may be synthetic.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C20) alkyl.

"Heteroalkyl," by itself or as part of another substituent refers to an alkyl in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR$^m$—, —PH—, —S(O)—, —S(O)$_2$—, —S(O)NR$^m$—, —S(O)$_2$NR$^m$—, and the like, including combinations thereof, where each R$^m$ is independently hydrogen or (C1-C6) alkyl.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Heteroarylalkyl" by itself or as part of another substituent refers to an acyclic alkyl group in which one of the hydrogen atoms bonded to a carbon atom, typically a terminal or sp³ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes 1-fluoromethyl, difluoromethyl, trifluoromethyl, 1-fluoroethyl, 1,1-difluoroethyl, 1,2-di fluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR″, "alkylamine" refers to a group of the formula NHR″ and "dialkylamine" refers to a group of the formula Nine, where each IV is independently an alkyl. As another example, "haloalkoxy" or "haloalkyloxy" refers to a group of the formula —OR$^P$, where R$^P$ is a haloalkyl.

5.3 Phenyl Xanthene Dyes

The phenyl xanthene dyes include any fluorescein, rhodol or rhodamine that comprises the C9 phenyl ring described herein. Accordingly, any rhodamine, rhodol and fluorescein type upper ring system may be employed. Suitable rhodamine type upper ring systems are described in U.S. Pat. No. 6,248,884, U.S. Pat. No. 6,229,055, U.S. Pat. No. 5,936,087, U.S. Pat. No. 5,847,162, U.S. Pat. No. 5,840,999, U.S. Pat. No. 5,750,409, U.S. Pat. No. 5,654,442, U.S. Pat. No. 5,442,045, U.S. Pat. No. 5,410,053, U.S. Pat. No. 5,366,860, U.S. Pat. No. 5,231,191, U.S. Pat. No. 5,188,934, U.S. Pat. No. 5,066,580, U.S. Pat. No. 4,481,136 and U.S. Pat. No. 4,439,356, all of which are incorporated herein by reference. However, the upper ring systems are not limited by these patents. As stated, any fluorescein, rhodol or rhodamine core upper ring system can be employed.

The C9 phenyl ring is substituted at one or both of carbons C11 or C15 with a group selected from alkyl, heteroalkyl, alkoxy, halo, haloalkyl, amino, alkylthio, cyano, isocyano, cyanato, mercaptocyanato, nitro, and sulfinyl. When both the C11 and C15 carbons are substituted, the substitutents may be the same or different. Thus, in one embodiment, the phenyl xanthene dyes include any fluorescein, rhodol, or rhodamine upper ring system that is substituted at the C9 carbon with a phenyl ring comprising the following structure:

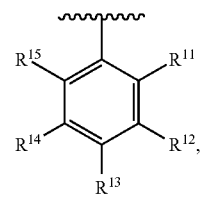

where at least one of $R^{11}$ or $R^{15}$ is selected from alkyl, heteroalkyl, alkoxy, halo, haloalkyl, amino, alkylthio, cyano, isocyano, cyanato, mercaptocyanato, nitro, and sulfinyl.

The remaining carbons on the C9 phenyl ring can, independently of one another, be unsubstituted or substituted with any group having no more than 40 atoms and typically no more than 25 atoms. Illustrative substituent groups that can be positioned at carbons C12, C13 and/or C14 include alkyl, heteroalkyl, aryl, heteroaryl, alkoxy, halo, haloalkyl, amino, alkylthio, cyano, isocyano, cyanato, mercaptocyanato, nitro, sulfinyl, sulfonyl, sulfonamide, carboxyl and carboxyamide. Accordingly, in another embodiment, at least one of $R^{11}$ or $R^{15}$ is substituted as described above and the remainder of $R^{11}$, $R^{12}$, $R^{13}$, $R^{14}$ and $R^{15}$ are, independently of one another, selected from hydrogen, alkyl, heteroalkyl, aryl, heteroaryl, alkoxy, halo, haloalkyl, amino, alkylthio, cyano, isocyano, cyanato, mercaptocyanato, nitro, sulfinyl, sulfonyl, sulfonamide, carboxyl and carboxyamide.

As long as at least one of $R^{11}$ and $R^{15}$ is substituted as described above, substituents at the remaining carbons in the C9 phenyl ring may be absent or present in any conceivable combination. This is illustrated by the following exemplary C9 phenyl structures, wherein one or both of $R^{11}$ and $R^{15}$ is $R^O$ and the remaining carbons on the phenyl are either unsubstituted or substituted with $R^S$, wherein each $R^O$, independently, is a group selected from alkyl, heteroalkyl, alkoxy, halo, haloalkyl, amino, alkylthio, cyano, isocyano, cyanato, mercaptocyanato, nitro, and sulfinyl, and each $R^S$, independently, is any substituent having up to 40 atoms.

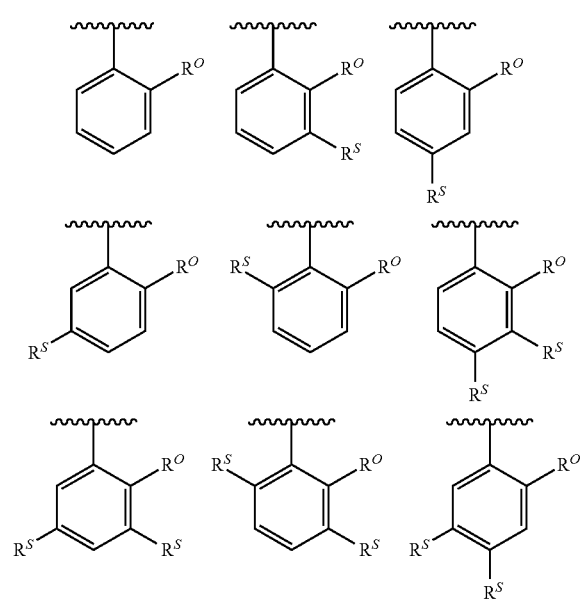

-continued

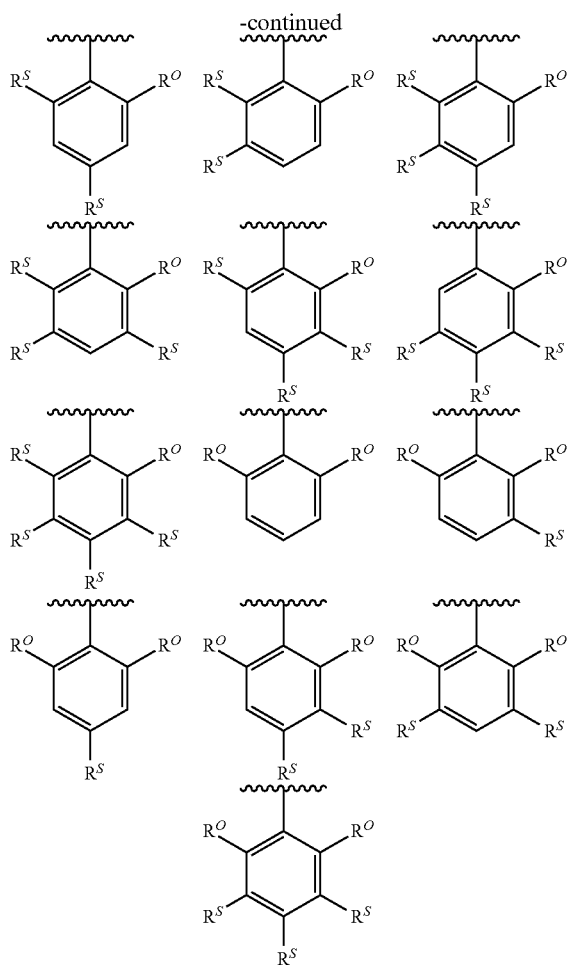

It has been discovered that xanthene dyes that include a C9 phenyl substituted with halo, haloalkyl, alkoxy and/or nitrile substituents exhibit especially good fluorescent properties, particularly when the substituents are placed at the C11 and/or C15 carbons. Accordingly, in another embodiment, at least one of $R^{11}$ and $R^{15}$ is selected from an alkoxy, halo, haloalkyl and/or nitrile. In yet another embodiment, $R^{11}$ and $R^{15}$ are each, independently of one another, an alkoxy, halo, haloalkyl and/or nitrile.

In still another embodiment, at least one of $R^{11}$ and $R^{15}$ is selected from an alkoxy, halo and/or haloalkyl and the remainder of $R^{11}$, $R^{12}$, $R^{13}$, $R^{14}$ and $R^{15}$ are, independently of one another, selected from hydrogen, alkoxy, halo and/or haloalkyl. In another embodiment, $R^{11}$ and $R^{15}$ are each, independently of one another, an alkoxy, halo and/or haloalkyl and the remainder of $R^{12}$, $R^{13}$ and $R^{14}$ are, independently of one another, selected from hydrogen, alkoxy, halo and/or haloalkyl. Any alkoxy and/or halo and/or haloalkyl group present on the lower phenyl ring may be the same or different. However, in one embodiment, any alkoxy and/or halo and/or halo alkyl group present on the lower phenyl ring is identical to any other alkoxy and/or halo and/or haloalkyl group present on the phenyl ring. Furthermore, in one embodiment, the lower phenyl ring is only substituted with hydrogen, alkoxy, halo and/or haloalkyl groups.

Especially suitable alkoxy groups include (C1 to C20) oxyalkyls, particularly methoxy. In one embodiment, the phenyl ring is only substituted with hydrogen and identical alkoxy groups. In one embodiment at least two groups on the phenyl ring are alkoxy. In another embodiment at least three groups on the phenyl ring are alkoxy. In another embodiment at least four groups on the phenyl ring are alkoxy. In another embodiment all of the groups on the phenyl ring are alkoxy.

Especially suitable halos include chloro and fluoro groups. In one embodiment, the phenyl ring is only substituted with hydrogen and identical halo groups, such as fluoro or chloro. In one embodiment at least two groups on the phenyl ring are halo. In another embodiment at least three groups on the phenyl ring are halo. In another embodiment at least four groups on the phenyl ring are halo. In another embodiment all of the groups on the phenyl ring are halo.

Especially suitable haloalkyls include —CF3. Accordingly, in one embodiment, the phenyl ring is only substituted with hydrogen and haloalkyl groups such as —CF3 groups. In one embodiment at least two groups on the pheny ring are haloalkyl. In another embodiment at least three groups on the phenyl ring are haloalkyl. In another embodiment at least four groups on the phenyl ring are alkoxy. In another embodiment all of the groups on the phenyl ring are haloalkyl.

Embodiments where the C9 phenyl ring is substituted at both the C11 and C15 carbons also exhibit especially good fluorescent properties. Accordingly, in one embodiment, $R^{11}$ and $R^{15}$ are each, independently of one another, selected from alkyl, heteroalkyl, alkoxy, halo, haloalkyl, amino, alkylthio, cyano, isocyano, cyanato, mercaptocyanato, nitro, and sulfinyl. The remaining carbons on the phenyl need not be substituted and, if substituted, the substituents may, independently, be the same or different when compared to $R^{11}$ and/or $R^{15}$.

Embodiments where the C9 phenyl ring is identically substituted at both carbons ortho to the point of the phenyl ring's attachment to the remainder of the xanthene dye also exhibit desirable fluorescent properties. Accordingly, in another embodiment, $R^{11}$ and $R^{15}$ are identical. Once again, the remaining carbons on the phenyl need not be substituted and, if substituted, the substituents may, independently, be the same or different when compared to $R^{11}$ and $R^{15}$. In one embodiment, any substituents on the lower phenyl ring are identical.

Symmetry appears to be an important factor in selecting optimal C9 phenyl rings. In this regard, the symmetry is relative to an imaginary axis running from the lower phenyl ring's point of attachment to the remainder of the xanthene dye (i.e., the 10-carbon) through a point para to the attachment (i.e., the 13-carbon). Accordingly, in one embodiment, $R^{11}$ and $R^{15}$ are identical and the remainder of $R^{12}$, $R^{13}$ and $R^{14}$ are, identically, either hydrogen or a substituent different from $R^{11}$ and $R^{15}$. In another embodiment $R^{11}$, $R^{13}$, and $R^{15}$ are identical and the remainder of $R^{12}$ and $R^{14}$ are, identically, either hydrogen or a substituent different from $R^{11}$, $R^{13}$ and $R^{15}$. In yet another embodiment, $R^{11}$, $R^{12}$, $R^{14}$ and $R^{15}$ are identical and $R^{13}$ is either hydrogen or a substituent different from $R^{11}$, $R^{12}$, $R^{14}$ and $R^{15}$. In still another embodiment, $R^{11}$, $R^{12}$, $R^{13}$, $R^{14}$ and $R^{15}$ are all identical. Optimal lower phenyl rings include those where the ring exhibits one of the aforementioned symmetries and $R^{11}$ and $R^{15}$ are selected from the same alkoxy and/or halo and/or haloalkyl group.

For the purposes of illustration, the following non-limiting examples of symmetrical halo and alkoxy substituted lower phenyl rings are provided, wherein X represents any halo group and $R^4$ represents a (C1 to C20) alkyl:

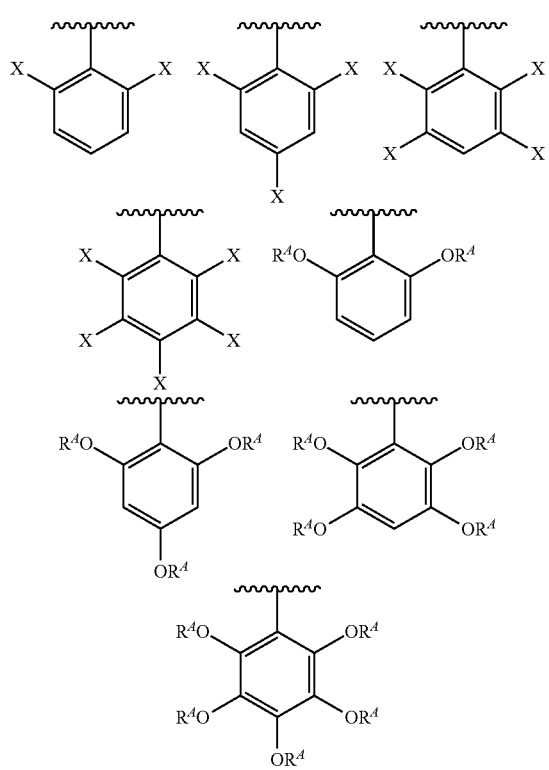

As stated, the fluorescent phenyl xanthene dyes comprise any fluorescein, rhodol or rhodamine that comprises the C9 phenyl ring discussed above. Illustrative phenyl xanthene dyes include dyes that comprise one of the following "core structures:"

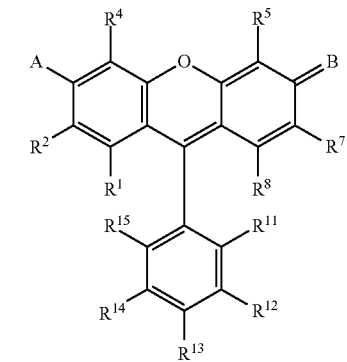

(I)

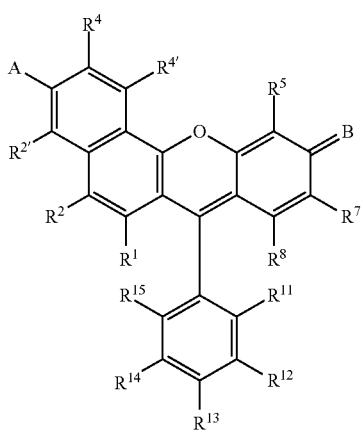

(II)

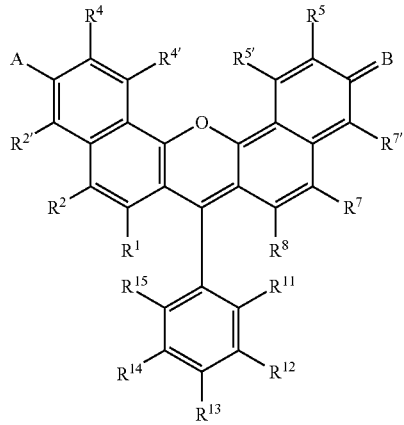

(III)

where A is —OH or NR$^{3'}$R$^{3''}$,
where B is a =O or =N$^{\oplus}$R$^{6'}$R$^{6''}$,
where R$^{11}$ and R$^{15}$ are selected from alkyl, heteroalkyl, alkoxy, halo, haloalkyl, amino, alkylthio, cyano, isocyano, cyanato, mercaptocyanato, nitro, and sulfinyl,
and the remainder of R$^1$, R$^2$, R$^{2'}$, R$^{3'}$, R$^{3''}$, R$^4$, R$^{4'}$, R$^5$, R$^{5'}$, R$^{6'}$, R$^{6''}$, R$^7$, R$^{7'}$, R$^8$, R$^{12}$, R$^{13}$, and R$^{14}$ are, independently, selected from hydrogen and a substituent having no more than 40 atoms, typically no more than 25 atoms.

In one embodiment the phenyl xanthene dyes are rhodamines, namely, when A is an amine group and B is an imminium group. In an alternative embodiment the phenyl xanthene dyes are rhodols, namely, when A is an amine and B is a oxo group. In an alternative embodiment, the phenyl xanthene dyes are fluoresceins, namely, when A is a hydroxyl group and B is a oxo group.

The signal emitted by the phenyl xanthene dyes can be tuned by the selection of different substituents. Especially beneficial substituents for tuning the phenyl xanthene dyes include R$^{11}$, R$^{12}$, R$^{13}$, R$^{14}$ and R$^{15}$, with R$^{11}$ and R$^{15}$ being exceptionally effective for tuning the dyes. The R$^2$, R$^{2'}$, R$^4$, R$^{4'}$, R$^5$, R$^{5'}$, R$^{7'}$ and R$^7$ substituents are also beneficial toward tuning the spectral properties of the dyes.

Usually, R$^1$ and R$^8$ are not, simultaneously, pendant or fused benzo, naphtho or polycyclic aryleno rings. The simultaneous presence of two relatively rigid aromatic substituents immediately next to the 9-carbon phenyl may generate steric hinderances.

As stated, symmetry can be an important factor in selecting optimal C9 phenyl rings. Symmetry can also be a factor in selecting optimal fluorescein, rhodol and rhodamine type upper ring systems, as well as a factor in selecting optimal phenyl xanthene dyes overall. Accordingly, it is desirable, but not necessary, for the phenyl xanthene dyes to have identical R$^{3'}$ and R$^{6'}$ substituents (if present) and/or identical R$^{3''}$ and R$^{6''}$ substituents (if present) and/or identical R$^4$ and R$^5$ substituents. Similarly, it is desirable, but not necessary, for the dyes to have identical R$^1$ and R$^8$ substituents and/or identical R$^2$ and R$^7$ substituents. Similarly, it is often desirable for R$^{11}$ and R$^{15}$, as well as R$^{12}$ and R$^{14'}$ to be identical. The presence of one or more, and especially all, of these symmetries facilitates the production of a strong signal.

In one embodiment, the phenyl xanthene dyes comprise core structure (I) and, additionally, the substituents therein are defined as follows:
A is selected from —OH and —NR$^{3'}$R$^{3''}$;
B is selected from =O and =N$^{\oplus}$R$^{6'}$R$^{6''}$;

$R^1$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^1$ may be taken together with $R^2$ to form part of a benzo, naptho or polycyclic aryleno group which is optionally substituted with one or more of the same or different $R^a$ or suitable $R^b$ groups;

$R^2$ is selected from hydrogen, $R^a$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^2$ may be taken together with $R^1$ to form part of a benzo, naptho or polycyclic aryleno group which is optionally substituted with one or more of the same or different $R^a$ or suitable $R^b$ groups, or, alternatively, when A is —$NR^{3'}R^{3''}$, $R^2$ may be taken together with $R^{3'}$ to form a 5- or 6-membered ring which is optionally substituted with one or more of the same or different $R^a$ or suitable $R^b$ groups;

$R^{3'}$, when present, is selected from hydrogen, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{3'}$ may be taken together with $R^2$ to form a 5- or 6-membered ring which is optionally substituted with one or more of the same or different $R^a$ or suitable $R^b$ groups;

$R^{3''}$, when present, is selected from (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^{3''}$ may be taken together with $R^4$ to form a 5- or 6-membered ring which is optionally substituted with one or more of the same or different $R^a$ or suitable $R^b$ groups;

$R^4$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, when B is —$NR^{3'}R^{3''}$, $R^4$ may be taken together with $R^{3''}$ to form a 5- or 6-membered ring which is optionally substituted with one or more of the same or different $R^a$ or suitable $R^b$ groups;

$R^5$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ group or, alternatively, when B is —$NR^{6'}R^{6''+}$, $R^5$ may be taken together with $R^{6''}$ to form a 5- or 6-membered ring which is optionally substituted with one or more of the same or different $R^a$ or suitable $R^b$ groups;

$R^{6''}$, when present, is selected from (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups or, alternatively $R^{6''}$ may be taken together with $R^5$ to form a 5- or 6-membered ring which is optionally substituted with one or more of the same or different $R^a$ or suitable $R^b$ groups;

$R^{6'}$, when present, is selected from hydrogen, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{6'}$ may be taken together with $R^7$ to form a 5- or 6-membered ring optionally substituted with one or more of the same or different $R^a$ or suitable $R^b$ groups;

$R^7$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or $R^b$ groups, or, alternatively, $R^7$ may be taken together with $R^8$ to form part of a benzo, naptho or polycyclic aryleno group which is optionally substituted with one or more of the same or different $R^a$ or suitable $R^b$ groups, or, alternatively, when B is —$NR^{6'}R^{6''+}$, $R^7$ may be taken together with $R^{6'}$ to form a 5- or 6-membered ring optionally substituted with one or more of the same or different $R^a$ or suitable $R^b$ groups;

$R^8$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable. $R^b$ groups and (C6-C40) arylalkyl or heteroaryl alkyl optionally substituted with one or more of the same or different $R^a$ or suitable. $R^b$ groups, or, alternatively, $R^8$ together with $R^7$ may form part of a benzo, naptho or polycyclic aryleno group which is optionally substituted with one or more of the same or different $R^a$ or suitable $R^b$ groups;

$R^{11}$ and $R^{15}$ are each, independently of one another, selected from halo, (C1-C20) alkyl, haloalkyl, —$OR^y$, —$SR^y$, —$SOR^y$, —$SO_2R^y$, and nitrile;

$R^{12}$, $R^{13}$ and $R^{14}$ are each, independently of one another, selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-

C40) arylalkyl or heteroarylalkyl optionally substituted with one or more of the same or different $R^a$ or suitable $R^b$ groups;

$R^x$ is selected from $-NR^cR^c$, $-OR^d$, $-SR^d$, halo, haloalkyl, $-CN$, $-NC$, $-OCN$, $-SCN$, $-NO$, $-NO_2$, $-N_3$, $-S(O)R^d$, $-S(O)_2R^d$, $-S(O)_2OR^d$, $-S(O)NR^cR^c$, $-S(O)_2NR^cR^c$, $-OS(O)R^d$, $-OS(O)_2R^d$, $-OS(O)_2OR^d$, $-OS(O)_2NR^cR^c$, $-C(O)R^d$, $-C(O)OR^d$, $-C(O)NR^cR^c$, $-C(NH)NR^cR^c$, $-OC(O)R^d$, $-OC(O)OR^d$, $-OC(O)NR^cR^c$ and $-OC(NH)NR^cR^c$;

$R^y$ is selected from (C1-C20) alkyls or heteroalkyls optionally substituted with lipophilic substituents, (C5-C20) aryls or heteroaryls optionally substituted with lipophilic substituents and (C2-C26) arylalkyl or heteroarylalkyls optionally substituted with lipophilic substituents;

$R^a$ is selected from hydrogen, (C1-C8) alkyl or heteroalkyl, (C5-C20) aryl or heteroaryl and (C6-C28) arylalkyl or heteroarylalkyl;

$R^b$ is selected from $-NR^cR^c$, $=O$, $-OR^d$, $=S$, $-SR^d$, $=NR^d$, $=NOR^d$, halo, haloalkyl, $-CN$, $-NC$, $-OCN$, $-SCN$, $-NO$, $-NO_2$, $=N_2$, $-N_3$, $-S(O)R^d$, $-S(O)_2R^d$, $-S(O)_2OR^d$, $-S(O)NR^cR^c$, $-S(O)_2NR^cR^c$, $-OS(O)R^d$, $-OS(O)_2R^d$, $-OS(O)_2OR^d$, $-OS(O)_2NR^cR^c$, $-C(O)R^d$, $-C(O)OR^d$, $-C(O)NR^cR^c$, $-C(NH)NR^cR^c$, $-OC(O)R^d$, $-OC(O)OR^d$, $-OC(O)NR^cR^c$ and $-OC(NH)NR^cR^c$;

each $R^c$ is independently hydrogen or $R^d$, or, alternatively, each $R^c$ is taken together with the nitrogen atom to which it is bonded to form a 5 to 8-membered saturated or unsaturated ring which may optionally include one or more of the same or different additional heteroatoms and which may optionally be substituted with one or more of the same or different $R^a$ or $R^d$ groups;

each $R^d$ is independently $R^a$ or $R^a$ substituted with one or more of the same or different $R^a$ or $R^e$ groups;

each $R^e$ is selected from $-NR^aR^a$, $=O$, $-OR^a$, $=S$, $=NR^a$, $=NOR^a$, halo, haloalkyl, $-CN$, $-NC$, $-OCN$, $-SCN$, $-NO$, $-NO_2$, $=N_2$, $-N_3$, $-S(O)R^a$, $-S(O)_2R^a$, $-S(O)_2OR^a$, $-S(O)NR^aR^a$, $-S(O)_2NR^aR^a$, $-OS(O)R^a$, $-OS(O)_2R^a$, $-OS(O)_2OR^a$, $-OS(O)_2NR^aR^a$, $-C(O)R^a$, $-C(O)OR^a$, $-C(O)NR^aR^a$, $-C(NH)NR^aR^a$, $-OC(O)R^a$, $-OC(O)OR^a$, $-OC(O)NR^aR^a$ and $-OC(NH)NR^aR^a$.

In another embodiment, the phenyl xanthene dyes comprise core structure (II) and, additionally, the substituents therein are defined as follows:

A is selected from $-OH$ and $-NR^{3'}R^{3''}$;

B is selected from $=O$ and $=N^{\oplus}R^{6'}R^{6''}$;

$R^1$, $R^{3''}$, $R^5$, $R^{6''}$, $R^{6'}$, $R^7$, $R^8$, $R^{11}$, $R^{12}$, $R^{13}$, $R^{14}$, $R^{15}$, $R^x$, $R^y$, $R^a$, $R^b$, $R^c$, $R^d$, and $R^e$ are as defined with respect to core structure (I), $R^2$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^2$ may be taken together with $R^1$ or $R^{2'}$ to form part of a benzo, naptho or polycyclic aryleno group which is optionally substituted with one or more of the same or different $R^a$ or suitable $R^b$ groups;

$R^{2'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^{2'}$ may be taken together with $R^2$ to form part of a benzo, naptho or polycyclic aryleno group which is optionally substituted with one or more of the same or different $R^a$ or suitable $R^b$ groups, or, alternatively, when A is $-NR^{3'}R^{3''}$, $R^{2'}$ may be taken together with $R^{3'}$ to form a 5- or 6-membered ring which is optionally substituted with one or more of the same or different $R^a$ or suitable $R^b$ groups;

$R^{3'}$, when present, is selected from hydrogen, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{3'}$ may be taken together with $R^{2'}$ to form a 5- or 6-membered ring which is optionally substituted with one or more of the same or different $R^a$ or suitable $R^b$ groups;

$R^4$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, when A is $NR^{3'}R^{3''}$, $R^4$ may be taken together with $R^{3''}$ to form a 5- or 6-membered ring which is optionally substituted with one or more of the same or different $R^a$ or suitable $R^b$ groups, or, alternatively, $R^4$ may be taken together with $R^{4'}$ to form part of a benzo, naptho or polycyclic aryleno group which is optionally substituted with one or more of the same or different $R^a$ or suitable $R^b$ groups; and $R^{4'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{4'}$ may be taken together with $R^4$ to form part of a benzo, naptho or polycyclic aryleno group which is optionally substituted with one or more of the same or different $R^a$ or suitable $R^b$ groups.

In another embodiment, the phenyl xanthene dyes comprise core structure (III) and, additionally, the substituents therein are defined as follows:

A is selected from $-OH$ and $-NR^{3'}R^{3''}$;

B is selected from $=O$ and $=N^{\oplus}R^{6'}R^{6''}$;

$R^1$, $R^{3''}$, $R^{6''}$, $R^8$, $R^{11}$, $R^{12}$, $R^{13}$, $R^{14}$, $R^{15}$, $R^x$, $R^y$, $R^a$, $R^b$, $R^c$, $R^d$, and $R^e$ are as defined with respect to core structure (I);

$R^2$, $R^{2'}$, $R^{3'}$, $R^4$, and $R^{4'}$ are as defined with respect to core structure (II);

$R^{5'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ group or, alternatively $R^5$ may be taken together with $R^5$ to form part of a benzo, naptho or polycyclic aryleno group which is optionally substituted with one or more of the same or different $R^a$ or suitable $R^b$ groups.

$R^5$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ group or, alternatively, when B is —$NR^{3'}R^{3''+}$, $R^5$ may be taken together with $R^{6''}$ to form a 5- or 6-membered ring which is optionally substituted with one or more of the same or different $R^a$ or suitable $R^b$ groups, or, alternatively, $R^5$ may be taken together with $R^{5'}$ to form part of a benzo, naptho or polycyclic aryleno group which is optionally substituted with one or more of the same or different $R^a$ or suitable $R^b$ groups;

$R^{6'}$, when present, is selected from hydrogen, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{6'}$ may be taken together with $R^{7'}$ to form a 5- or 6-membered ring optionally substituted with one or more of the same or different $R^a$ or suitable $R^b$ groups;

$R^{7'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or $R^b$ groups, or, alternatively, when B is —$NR^{3'}R^{3'+}$, $R^{7'}$ may be taken together with $R^{6'}$ to form a 5- or 6-membered ring optionally substituted with one or more of the same or different $R^a$ or suitable $R^b$ groups, or, alternatively, $R^{7'}$ may be taken together with $R^7$ to form part of a benzo, naptho or polycyclic aryleno group which is optionally substituted with one or more of the same or different $R^a$ or suitable $R^b$ groups; and $R^7$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or $R^b$ groups, or, alternatively, $R^7$ may be taken together with $R^{7'}$ or $R^8$ to form part of a benzo, naptho or polycyclic aryleno group which is optionally substituted with one or more of the same or different $R^a$ or suitable $R^b$ groups.

The list of possible phenyl xanthene dyes is as endless as the variations that can exist in the upper ring system. However, preferred dyes are fluoresceins, rhodols and rhodamines that have found most use in the industry, as modified to contain the C9 phenyl ring discussed above.

Along this line, the following fluoresceins, rhodols and rhodamines are noted: Rhodamine 101, Rhodamine 110, Rhodamine 6G, TAMRA, ROX, HEX, NAN, FLAN, TET, JOE, and ZOE. Those skilled in the art will be able to name many more commercially important fluoresceins, rhodamines and rhodols. Any fluorescein, rhodamine or rhodol can be modified at the C9 position to contain the lower phenyl ring.

5.4 Lipid Soluble Phenyl Xanthene Dyes

In one embodiment, the phenyl xanthene dyes not only contain the new lower phenyl ring but also contain sufficient lipophilic groups to make the phenyl xanthenes lipid soluble. This is especially beneficial when the phenyl xanthene dyes are used, for example, to imbibe hydrophobic polymeric particles that are useful in aqueous assays. Such embodiments are described, for example, in copending patent, application Ser. No. 10/837,983 filed May 4, 2004, which issued as U.S. Pat. No. 7,432,298 on Oct. 7, 2008, entitled "Fluorescent Polymeric Materials Containing Lipid Soluble Rhodamine Dyes," the disclosure of which is incorporated herein by reference.

Non-limiting examples of such polymeric particles include crosslinked and uncrosslinked polystyrene particles and styrene-(meth) acrylic acid copolymers. An unlimited variety of particles for use in assays are commercially available, including particles that are functionalized and/or paramagnetic and/or conjugated with a biological reagents. For example, Bangs Laboratories sells the following products: "plain (hydrophobic) polystyrene microspheres" of various sizes (catalog codes PS02N, PS03N, PS04N, PS05N, PS06N, PS07N, PS08N, PS00N); "carboxylate-modified microspheres" of various sizes (catalog codes PC02N, PC03N, PC04N, PC05N, PC06N, PC07N, PC08N and PC00N); "amino-modified microspheres" of various sizes (catalog codes PA02N, PA03N, PA04N, PA05N, PA06N, and PA00N); "classical magnetic microspheres" having carboxlic or amino functionality (catalog codes MC02N, MC03N, MC04N, MC05N, and MC00N); "encapsulated magnetic microspheres" with carboxylic and amino surface groups (catalog codes ME01N, ME02N, ME03N, and ME00N); and "protein-activated" or "protein-coated" microspheres (catalog codes CM01N, CM02N, CM03N, CP01N, CP02N and CP03N). Similarly, Dynal sells Dynabeads® which are uniform, superparamagnetic, monodisperse polymer beads that can either be uncoated or precoated with specific ligands. Dynabeads® are available in three different sizes, namely, 1 µm (Dynabeads® MyOne™ Streptavidin), 2.8 µm (Dynabeads® M-280 and Dynabeads® M-270) and 4.5 µm (Dynabeads® M-450 and Dynabeads® M-500).

In such embodiments, the degree of lipid solubility required for the phenyl xanthene dye necessarily varies as a function of the polymer utilized, the aqueous solvent or solvent system employed in the assay in which the polymeric particle is to be used, and the conditions (e.g., time, temperature, pressure, pH, etc.) under which the assay is run. Suitable degrees of lipid solubility are easily determined by methods known in the art. For example, suitable lipid solubility can be determined by a partition test wherein a known quantity of dye in organic solvent is combined with the aqueous solvent or solvent system used in the assay. If a partition results and, under the conditions used in the assay, there is no appreciable crossing by the dye into the solvent or solvent system, then the dye is sufficiently lipid soluble. Put another way, the lipid soluble phenyl xanthene dye should be sufficiently lipid soluble such that it is capable of being imbibed into the polymer when dissolved in an organic solvent or solvent system and, when the dyed polymer is subjected to the aqueous conditions of the assay, the dye should resist leaching out of the polymer to any degree that significantly impacts the fluorescent signature of the dye imbibed polymer or the results of the assay.

In those embodiments where the phenyl xanthene dyes are lipid soluble rhodamines, one or both of the exocyclic amine and exocyclic imminium nitrogens are often substituted with a lipophilic group designed to impart to the rhodamine lipophilic characteristics or properties. Thus, useful dyes include rhodamines that comprise the C9 phenyl ring described above and additionally comprise one or two lipophilic substituents at the exocyclic amine nitrogen and/or one or two lipophilic substituents at the exocyclic imminium nitrogen. In one embodiment, both the exocyclic amine nitrogen and the exocyclic imminium nitrogen are substituted with a lipophilic group. In another embodiment, the exocyclic amine nitrogen and the exocyclic imminium nitrogen are both substituted with two lipophilic groups. The lipophilic groups, whether attached to the same or different exocyclic nitrogen, may be the same or different. In one embodiment, the lipophilic groups on the exocyclic nitrogens are the same.

In those embodiments where the phenyl xanthene dyes are lipid soluble rhodols, the exocyclic amine nitrogen is often substituted with a lipophilic group designed to impart to the rhodol lipophilic characteristics or properties. Thus, useful dyes include rhodols that comprise the C9 phenyl ring described above and also comprise one or two lipophilic substituents at the exocyclic amine nitrogen. In one embodiment, the exocyclic amine nitrogen is substituted with one lipophilic group. In another embodiment, the exocyclic amine nitrogen is substituted with two lipophilic groups. If there are two lipophilic groups on the exocyclic amine nitrogen, the lipophilic groups may be same or different. In one embodiment, there are two lipophilic groups on the exocyclic amine nitrogen that are the same.

Lipid-soluble phenyl xanthenes may include lipophilic substituents at other positions, as well. It is the net effect of the lipophilic substituents that determines whether the phenyl xanthene dye is lipid soluble. This is especially true for fluoresceins which have no exocyclic amine or imminium nitrogens.

Lipophilic substituents are groups that impart the resultant phenyl xanthene dye with lipophilic characteristics or properties as denoted above. The nature of each lipophilic substituent is not critical, as long as the resultant phenyl xanthene dye is lipid soluble. Non-limiting examples of suitable lipophilic substituents include unsubstituted (C4-C20) alkyls, (C5-C40) aryls, and (C6-C40) arylalkyls. Depending on the number of methylene and methine units in the lipophilic substituent, the lipophilic substituent may also include pendant or internal polar or hydrophilic groups. For example, a lipophilic substituent may include one or more internal heteroatoms, such as one or more internal O, S, N or NH groups. As another example, a lipophilic substituent may include one or more pendant polar or hydrophilic substituents, such as one or more pendant halogen, —OH, —SH, —NH$_2$, —C(O)OH, —C(O)NH$_2$ or other polar or hydrophilic groups. Thus, lipophilic substituents may also include substituted (C4-C20) alkyl, substituted (C5-C40) aryls and substituted (C6-C40) arylalkyls, as well as substituted and unsubstituted (C4-C20) heteroalkyl, substituted and unsubstituted (C5-C40) heteroaryls and substituted and unsubstituted (C6-C40) arylalkyls. The number of internal or pendant polar or hydrophilic groups that may be included in a lipophilic substituent will depend upon, among other factors, the number of methylene or methine groups included in the lipophilic substituent and number of lipophilic substituents on the phenyl xanthene dye. The nature and number of lipophilic groups necessary to make a phenyl xanthene lipid soluble can vary from molecule to molecule, and will be apparent to those of skill in the art.

5.5 Conjugatable Phenyl Xanthene Dyes

Oftentimes, it is desirable to attach fluorescent dyes such as the phenyl xanthene dyes described herein to substances such as solid supports, particles, and biological and non-biological molecules (e.g., drugs, amino acids, peptides, polypeptides, proteins, nucleosides, nucleotides, oligonucleotides, polynucleotides, carbohydrates, etc.) Thus, in one embodiment, the various phenyl xanthene dyes described herein include one or more moieties suitable for such attachment. Such moieties are expressed by the formula —S-LG where S is a direct bond or a spacing moiety and LG is a linking group capable of forming a linkage with the substance to be conjugated.

The linking group LG may be any moiety capable of forming the linkage, which may be covalent or non-covalent. For example, the linking group may be one member of a pair of specific binding molecules that non-covalently bind one another, such as biotin and avidinstreptavidin. Thus, in one embodiment, the linking group is biotin. Alternatively, the linking group may be a functional group capable of forming a covalent linkage with a "complementary" functional group, such as an electrophilic (or nucleophilic) group which is capable of forming a covalent linkage with a complementary nucleophilic (or electrophilic) group, although other groups may be used depending on the desired linking chemistry, as is well known in the art. Non-limiting examples of suitable electrophilic linking groups include any one or a combination of the following: aminesanilines, alcoholsphenols, thiols, hydrazines and hydroxylamines. Non-limiting examples of suitable electrophilic linking groups include any one or a combination of the following: activated esters such as pentafluorophenyl ester and NHS-ester, acrylamides, acyl azides, acyl halides, acyl nitriles, aldehydes, ketones, alkyl halides, alkyl sulfonates, anhydrides, aryl halides, aziridines, boronates, carboxylic acids, carbodiimides, diazoalkenes, epoxides, haloacetamides, halotriazines, imido esters, isocyanates, isothiocyanates, maleimides, phosphoamidites, silyl halides, sulfonate esters and sulfonyl esters.

The linking group may be attached directly to the phenyl xanthene dye or it may be spaced away from the phenyl xanthene dye by way of spacing moiety "S." As will be appreciated by skilled artisans, the nature and composition of the spacing moiety is not critical and may depend upon the particular application. Thus, the spacing moiety may comprise virtually any combination of atoms or groups commonly employed to space one molecule from another.

As a specific example, the spacing moiety may be selected from substituted or unsubstituted alkylenes or heteroalkylenes, substituted or unsubstituted arylenes or heteroarylenes, substituted or unsubstituted arylalkylenes or heteroarylalkylenes, or a combination of such groups. In one embodiment, the spacing moiety is an unsubstituted alkylene of the formula —$(CH_2)_n$—, where n is an integer ranging from 1 to 40, typically from 1 to 20 and more typically from 1 to 10. Other exemplary spacing moieties and linking groups are described, for example, in U.S. Pat. Nos. 4,439,356, 4,481,136, 5,188,934, 5,654,442, 5,863,727, 5,847,162, 6,229,055, 6,248,884 and 6,372,907.

The linking group, whether attached directly or spaced away via spacing moiety "S," may be attached to any available position of the phenyl xanthene dye. For example, the linking group may be attached to any available position on the upper ring system or the lower ring. In one embodiment, the linking group —S-LG is attached to the C2, C4, C5, or C7 position of the upper ring system. In another embodiment, the linking group —S-LG is attached to the C12, C13 or C14 position of the lower ring.

In one embodiment, a phenyl xanthene suitable for covalent attachment comprises any of the previously-described phenyl xanthenes wherein one or more of $R^1$, $R^2$, $R^{2'}$, $R^4$, $R^{4'}$, $R^5$, $R^{5'}$, $R^7$, $R^{7'}$, $R^8$, $R^{11}$, $R^{12}$, $R^{13}$, $R^{14}$ or $R^{15}$ is a substituent of the formula —S-LG, where S is a direct bond or a spacing moiety and LG represents a linking group. In a specific embodiment, one of $R^4$, $R^5$, $R^{12}$, $R^{13}$ or $R^{14}$ is S-LG.

5.6 Conjugated Phenyl Xanthene Dyes

The lipid-soluble rhodamine dyes may be linked to another substance. In this embodiment, at least one substituent on the phenyl xanthene dye is —$S^1$-LK-$S^2$—CS. In this case, CS represents the conjugated substance and $S^1$, LK and $S^2$ form what is known in the art as a "linker"—which embraces any functionality known in the art that attaches a dye to another substance.

$S^1$ and $S^2$ are, independently of one another, a covalent bond or a spacing moiety. The nature of the spacing moieties $S^1$ and $S^2$ may vary broadly. Illustrative spacing moieties include those previously specified for the spacing moiety "S."

LK represents a linkage, which may be a bond or another type of linkage, such as a linkage formed between a nucleophilic (or electrophilic) group and a complementary electrophilic (or nucleophilic) group. In one embodiment, LK is selected from an ester, an amide, a sulfonamide, a hydrazine, an imine, a maleimide, a sulfide, a disulfide, a carbamate and a thiocarbamate linkage.

The linker will vary depending the identity of the conjugated substance. Illustrative linkers are provided, for example, in U.S. Pat. Nos. 4,439,356, 4,481,136, 5,188,934, 5,654,442, 5,863,727, 5,847,162, 6,229,055, 6,248,884 and 6,372,907.

In one exemplary embodiment, a conjugated phenyl xanthene is any of the previously-described phenyl xanthenes in which one or more of $R^1$, $R^2$, $R^{2'}$, $R^4$, $R^{4'}$, $R^5$, $R^{5'}$, $R^7$, $R^{7'}$, $R^8$, $R^{11}$, $R^{12}$, $R^{13}$, $R^{14}$ or $R^{15}$ is a substituent of the formula —$S^1$-LK-$S^2$—CS. In a specific embodiment, one of $R^4$, $R^5$, $R^{12}$, $R^{13}$ or $R^{14}$ is —$S^1$-LK-$S^2$—CS.

5.7 Energy Transfer Dyes

In another embodiment, the phenyl xanthene dye is part of an energy transfer ("ET") network comprising, for example, from two to four dyes covalently attached to one another that transfer energy to generate a longer Stoke's shift. In other words, the phenyl xanthene dye may be part of series of dyes that are covalently attached to one another. One example of an ET network would be a fluorescence resonance energy transfer ("FRET") dye. In this embodiment, at least one substituent on the phenyl xanthene dye is selected from —$S^1$-LK-$S^2$-D, where $S^1$, $S^2$ and LK are as previously defined and D is another dye in the network. In one embodiment, each dye in the energy transfer network is within 5 to 100 Å of the neighboring dye or dyes in the network to which it is covalently attached. In such embodiments, the phenyl xanthene dye can be the donor, acceptor, or an intermediate dye in the network.

In one embodiment, an energy transfer dye comprises any of the previously-described phenyl xanthenes in which one or more of $R^1$, $R^2$, $R^{2'}$, $R^4$, $R^{4'}$, $R^5$, $R^{5'}$, $R^7$, $R^{7'}$, $R^8$, $R^{11}$, $R^{12}$, $R^{13}$, $R^{14}$ or $R^{15}$ is a substituent of the formula —$S^1$-LK-$S^2$-D. In a specific embodiment, one of $R^4$, $R^5$, $R^{12}$, $R^{13}$ or $R^{14}$ is —$S^1$-LK-$S^2$-D.

The identity of donor or acceptor dye is not critical, so long as it can donate or accept energy from or to the particular phenyl xanthene to which it is attached. Dyes that can act as donor or acceptors for phenyl xanthenes are well-known, and include, for example, other fluoresceins, rhodamines, and rhodols, as well as cyanines, phthalocyanine and squaraine dyes. Any of these dyes, or another phenyl xanthene as described herein, may be used as the donor dye or acceptor dye in an energy transfer dye comprising the phenyl xanthene. The ability to select a suitable dye for a particular phenyl xanthene is within the routine skill in the art.

As will be appreciated by skilled artisans, the various substituents $S^1$, LK and S of the linker should be selected to position the lipid-soluble rhodamine and acceptor or donor dye in close enough proximity to one another such that the dyes can undergo energy transfer, whether via FRET or another mechanism.

Suitable linkers are illustrated, for example, by U.S. Pat. Nos. 5,800,996 and 5,863,727, issued to Lee et al., U.S. Pat. No. 6,008,279, issued to Benson et al., and U.S. Pat. No. 5,654,419, issued to Mathies et al., all of which are hereby incorporated by reference. Methods of synthesizing such energy transfer dyes, as well as suitable points of attachment for covalently coupling the lipid-soluble rhodamine and acceptor or donor dye D to one another are also described in these patents.

In one exemplary embodiment, an energy transfer dye of the formula $D^1$-$S^1$-LK-$S^2$-$D^2$, where $D^1$ represents a phenyl xanthene dye, D represents another dye, and $S^1$, LK, and $S^2$ are as defined above, may be synthesized by reacting a phenyl xanthene of the formula $D^1$-$S^1$-LG, where LG represents a linking group, with a donor or acceptor dye of the formula $D^2$-$S^2$-LG', where LG' represents a linking group which is complementary to linking group LG such that LG and LG' may react with one another to form linkage LK. As a specific embodiment, LG may be an activated ester such as an NHS-ester and LG' may be a primary amino group, such that reaction forms an amide linkage LK.

5.8 Method for Synthesizing Phenyl Xanthene Dyes

Phenyl xanthene dyes which include a C9-phenyl moiety which does not have an ortho carboxylate or sulfonate substituent may be prepared by methods that are illustrated and described in the figures and examples, respectively, provided herein. In general, an ortho substituted benzaldehyde, which may or may not be further substituted, is reacted with either a substituted or unsubstituted 3-amino-1-hydroxybenzene or a substituted or unsubstituted 1,3-dihydroxybenzene or a mixture thereof. This is visually illustrated below:

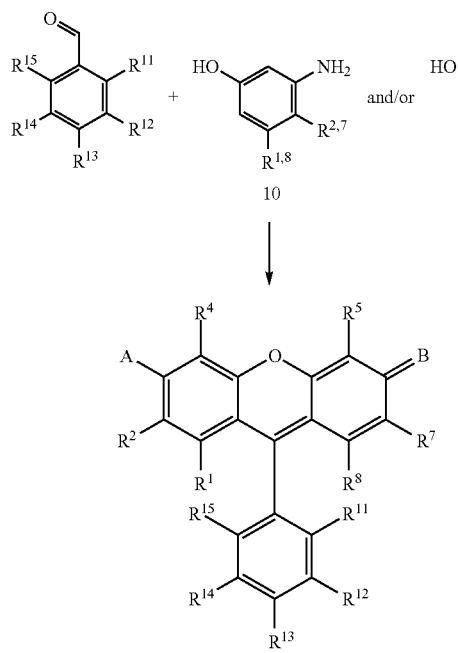

where A is an amino or hydroxyl group, depending on whether it arises from compound 10 or 20 respectively, where B is an imminium or an oxo group, depending on whether it arises from compound 10 or 20 respectively, and where the amine on compound 10 may be further substituted with any desirable substituents for $R^{3'}$, $R^{3''}$, $R^{6'}$ and $R^{6''}$.

The reaction is carried out in solution, for example suspended in 1,2-dichlorbenzene. The reaction is carried out under heat. Generally, a temperature ranging from 160 to 170° C. will suffice. Preferably, a catalyst is employed. For reactions utilizing substituted or unsubstituted 3-amino-1-hydroxybenzene, lithium perchlorate is a good catalyst. For reactions employing 1,3-dihydroxyphenol, toluene sulfonic acid is a good catalyst. Under these conditions, the reaction takes about 60 minutes to complete.

Suitable aminophenol and benzaldehyde compounds are commercially available and easily isolated or synthesized by one of skill in the art. For example, benzaldehyde can be made by partial reduction of a benzoic acid, amide, or nitrile. Similarly, 3-amino-1-hydroxybenzene can be manufactured by the reduction of nitrophenol as described in U.S. Pat. No. 3,079,435. Dihydroxy rescorcinol and the like are commercially available from Aldrich Chemical Company.

Extended phenyl xanthenes can be made by utilizing amino-hydroxy substituted naphthalenes and/or dihydroxy substituted naphthalenes in conjunction with the 3-amino-1-hydroxybenzenes and 1,2-dihydroxybenzenes discussed above. This reaction is visually illustrated below:

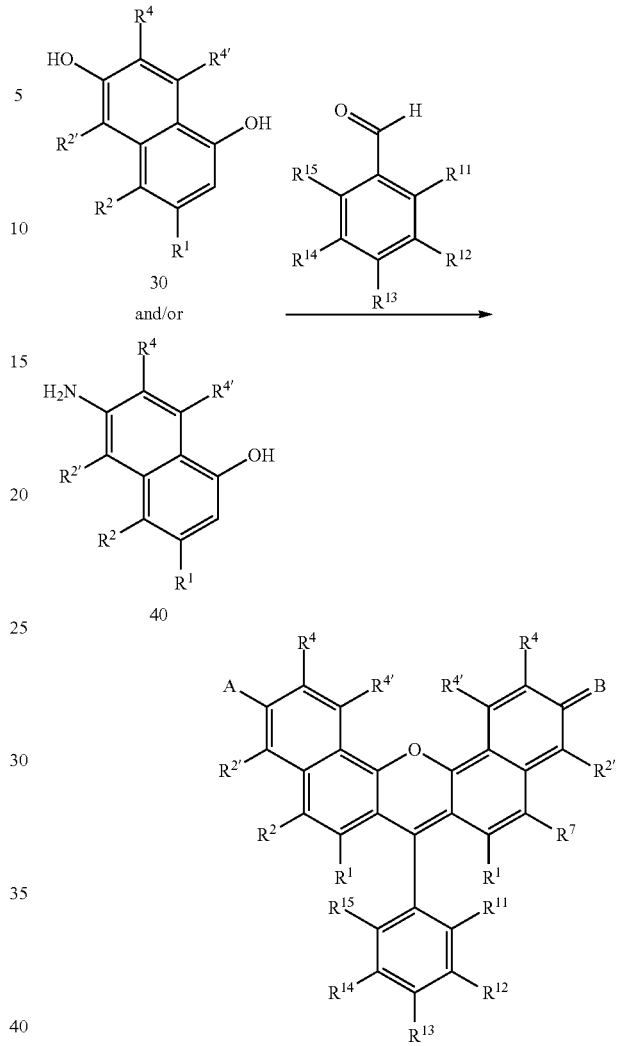

where A is an hydroxy or amino group, depending on whether it arises from compound 30 or 40 respectively, where B is an oxo or an imminium group, depending on whether it arises from compound 30 or 40 respectively, and where the amine on compound 40 may be further substituted with any desirable substituents for $R^{3'}$, $R^{3''}$, $R^{6'}$ and $R^{6''}$.

5.9 Improved Properties

The phenyl xanthene dyes described herein, when excited by a light source, emit an unusually strong spectral signal with low background noise. Lipid soluble embodiments of the xanthene dyes are easily imbibed into, and retained by, hydrophobic polymeric particles, even in the presence of water based solvents. Finally, the rhodamine dyes are highly photo and chemically stable. In fact, some of the rhodamine dyes have photostabilities ten times that of fluorescein and 100 times that of cyanine.

5.10 Illustrative Uses

The phenyl xanthene dyes of the instant invention have direct applications in a number of technologies, including use as fluorescent labels in automated DNA sequencing, oligonucleotide hybridization methods, detection of polymerase-chain reaction products, immunoassays, and the like. For many applications, multiple dyes are employed, in combination, to permit multiplex fluorescent detection.

The phenyl xanthene dyes can be used to sequence nucleic acids for example using the Sanger method. The specifics of sequencing nucleic acids by the Sanger method are well-known in the art and are not repeated here. For such sequencing applications, the phenyl xanthene dyes described herein may be attached to the primer or to a terminating nucleotide, such as a 2,3'-dideoxynucleotide triphosphate. Examples of various labeled primers, labeled terminating nucleotides and methods of using such labeled primers and terminating nucleotides in sequencing and other applications are described in U.S. Pat. Nos. 5,188,934, 5,366,860, 5,654, 442, 5,800,996, 5,840,999, 5,847,162, 5,863,727, 5,936,087, 6,008,379, 6,248,884 and 6,372,907, the disclosures of which are incorporated herein by reference. The xanthene dyes described herein may be attached to similar primers and terminating nucleotides and used in an analogous manner.

Alternatively, the phenyl xanthene dyes can be imbibed into particles used in the passive or covalent coupling of analytes. In a particularly preferred aspect of the invention, a mixture of lipid soluble phenyl xanthenes and, optionally additional dyes, are internally incorporated, simultaneously or sequentially, into polymeric microparticles to give the microparticles a unique spectral signature or "bar code." A number of particle populations are created, each characterized by a different spectral bar code. The particles can then be activated or otherwise modified so that they have a specific reactivity with one or more analytes in a clinical or test sample. Thus, the spectral bar code in each particle population corresponds to a different known reactivity. The particle populations can then be blended in a specified ratio to form a multicolored particle mixture which is then contacted with the analyte. Imbibed bead mixtures may contain hundreds to thousands of fluorescent dye molecules which greatly increases the sensitivity of assays employing bead labels in comparison to single dye assays.

To achieve truly multiplexed analysis of a plurality of analytes in a single sample, some sort of additional marker is necessary to show that a positive event has occurred on a particle. This additional marker can be many things, for example, it can be a molecule, such as biotin, which is detectable by its interaction with another compound, in this example streptavidin. Alternatively, the additional marker can be second fluorescent signal, e.g., a green fluorescent label. The marker is often provided by a labeling reagent which is also capable of binding to the analyte of interest:

5.11 Inherent Limitations in Structures

Those skilled in the art will appreciate that many of the phenyl xanthene dye compounds described in the various structures herein may exhibit the phenomena of tautomerism, conformational isomerism, geometric isomerism and/or stereo isomerism. As the structures presented in the specification and claims can represent only one tautomeric, conformational isomeric, enantiomeric or geometric isomeric form, it should be understood that the invention encompasses any tautomeric, conformational isomeric, enantiomeric and/or geometric isomeric forms of the compounds that have one or more of the utilities described herein. As a specific example, reference is made throughout the specification to the C3 amino and C6 imminium substituents in rhodamines and rhodols. As this nomenclature corresponds to the illustrated structures, which represent only one of several possible tautomeric forms (or resonance structures) of the compounds, it will be understood that these references are for convenience only and that any such references are not intended to limit the scope of the compounds described herein.

Furthermore, those of skill in the art will recognize that the phenyl xanthene dyes of the invention may exist in many different protonation states, depending on, among other things, the pH of their environment. The structures provided herein depict the compounds in only one of several possible protonation states. Accordingly, it will be understood that these structures are illustrative only, and that the invention is not limited to any particular protonation state—any and all protonated forms of the dyes are intended to fall within the scope of the invention.

As the phenyl xanthene dye compounds used in the invention may bear positive and negative charges, depending upon their physical state, they often have counterions associated therewith. The identity or identities of any associated counterions is typically dictated by the synthesis and/or isolation methods by which the compounds are obtained. Typical counterions include, but are not limited to, halides, acetate, trifluoroacetate, any salt of a strong acid, and mixtures thereof. It will be understood that the identity or identities of any associated counterions are not a critical feature of the invention and that the invention encompasses the use of dyes in association with any type of counter ion. Moreover, as the compounds can exists in a variety of different forms, the invention is intended to encompass not only forms of the dyes that are in association with counterions (e.g., dry salts), but also forms that are not in association with counterions (e.g., aqueous or Organic solutions).

5.12 Incorporation by Reference

All publications, patents and patent applications mentioned in this specification are herein incorporated by reference to the same extent as if each individual publication, patent or patent application was specifically and individually indicated to be incorporated by reference. No admission is made that any reference cited in this specification is prior art.

6. EXAMPLES 6.1 Overview of Synthesis for Fluorescein, Rhodol and Rhodamine Dyes Exemplary phenyl xanthenes were synthesized from reactions of substituted and unsubstituted 1-hydroxy-3-aminobenzene derivatives and/or substituted and unsubstituted 1,3 dihydroxybenzene derivatives with phenyl aldehyde derivatives. Dye structures were verified by mass spectrometry.

6.2 Example 1

As illustrated in FIG. 1A, phenyl xanthenes containing symmetrically substituted upper ring systems were made by reacting one or more 3-amino-1-hydroxy-benzenes 120 (where $Y^{A,B}$ is an amine) and/or one or more 1,3-dihydroxybenzene 120 (where $Y^{A,B}$ is a hydroxyl) with a phenyl aldehyde of general structure 130. Reactants were suspended in a high boiling solvent, such as dichlorobenzene in the presence of a catalyst. Acid catalysts, such as toluene sulfonic acid, are used when $Y^{A,B}$ is a hydroxyl. Catalysts such as lithium perchlorate are used when $Y^{A,B}$ is an amine. Reactants were heated and stirred for 1 to 5 hours at a temperature from 130° to 155° C.

By this method, dyes corresponding to structure 140 were made:

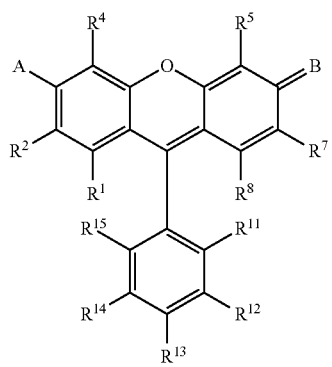

140 where $R^1=R^8$, $R^2=R^7$ and $R^4=R^5$. Symmetrically substituted rhodamines were produced by reacting a 3-amino-1-hydroxy-benzene with a benzaldehyde in the presence of lithium perchlorate. Symmetrically substituted fluoresceins were produced by reacting a 1,3-dihydroxy-benzene with a benzaldehyde in the presence of toluene sulfonic acid.

Phenyl xanthenes with non-symmetrically substituted upper ring systems can also be produced by employing multiple 3-amino-1-hydroxy-benzenes and/or multiple 1,3-dihydroxybenzenes that contain different substituents.

Dyes that were made by this procedure include the following:

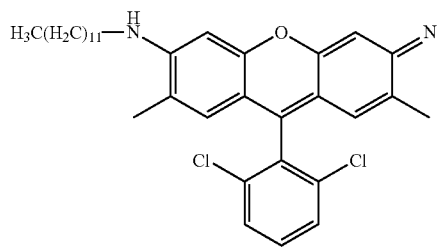

Dye (3)

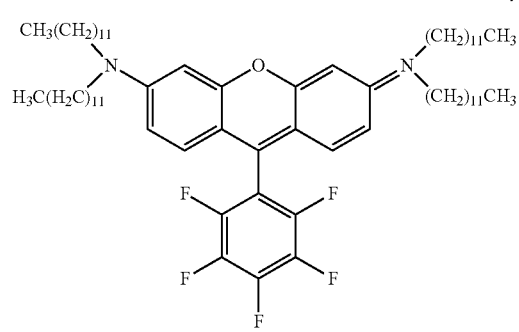

Dye (7)

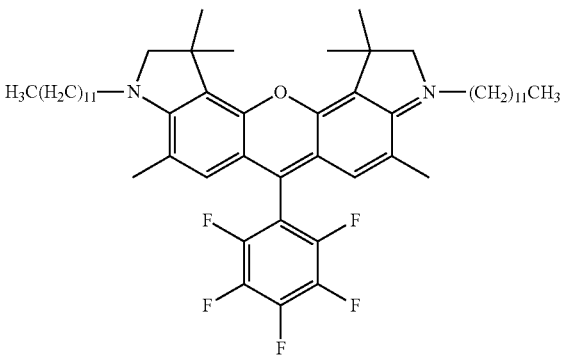

Dye (10)

6.3 Example 2

As illustrated in FIG. 2A, phenyl xanthenes with symmetrically substituted and symmetrically extended upper ring systems were made by reacting an amino-hydroxy-substituted napthalene 220 (where $Y^{A,B}$ is an amine) and/or a dihydroxy substituted naphthalene 220 (where $Y^{A,B}$ is a hydroxyl) with a phenyl aldehyde of general structure 130. Reactants were suspended in a high boiling solvent, such as dichlorobenzene, in the presence of a catalyst. Acid catalysts, such as toluene sulfonic acid, are used when $Y^{A,B}$ is a hydroxyl. Catalysts such as lithium perchlorate are used when $Y^{A,B}$ is an amine. Reactants were heated and stirred for 1 to 5 hours at a temperature from 130° to 155° C.

By this method, symmetrically extended phenyl xanthene dyes corresponding to structure 240 were made:

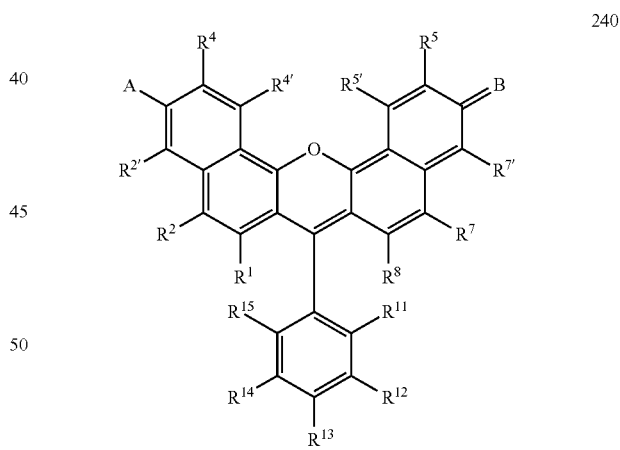

240 where $R^1=R^8$, $R^2=R^7$, $R^{2'}=R^{7'}$, $R^4=R^5$, and $R^{4'}=R^{5'}$. Symmetrically extended and symmetrically substituted rhodamines were produced by reacting an amino-hydroxy-substituted napthalene with a benzaldehyde in the presence of an toluene suflonic acid. Symmetrically extended and symmetrically substituted fluoresceins were produced by reacting a dihydroxy substituted naphthalene with a benzaldehyde in the presence of lithium perchlorate.

As illustrated in FIG. 2B, phenyl xanthenes with non-symmetrically extended upper ring systems can be synthesized by the same procedure if an additional reactant, namely a 3-amino-1-hydroxy-benzene (where $Y^{A,B}$ is an amine) and/or a 1,3-dihydroxy-benzene 120 (where $Y^{A,B}$ is a hydroxyl), is added to the reaction mixture.

Furthermore, phenyl xanthene dyes with non-symmetrically substituted upper ring systems can be synthesized by using a mixture of reactants with varying substituents as previously described.

Dyes that were made by this procedure include the following:

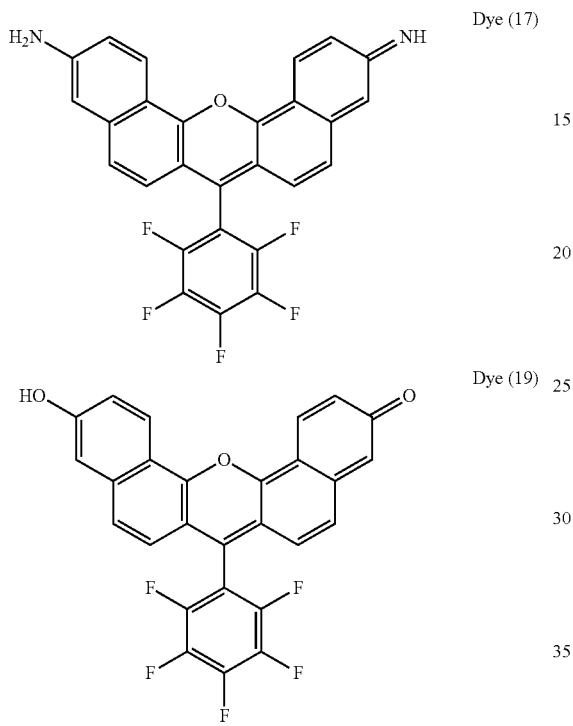

6.4 Example 3

Flourescein dyes of structure 340 were synthesized in reactions of dihydroxy benzene derivatives 320 and benzoate ester derivatives 100 as outlined in FIG. 3. Derivatives of 320 were synthesized by established procedures (see U.S. Pat. Nos. 5,188,934 and 6,008,379). As a general dye synthesis procedure 120 and benzoate ester 130 were suspended in neat methane sulfonic acid and the reaction heated at 130° C. for 3 hours. The reaction mixture was precipitated by pouring into ice, the solid precipitate collected by filtration, the crude dye 340 suspended in $CH_2Cl_2$/MeOH/AcOH (95:5:0.5), and loaded into a silica gel column. The column was first eluted with $CH_2Cl_2$/MeOH/AcOH (95:5:0.5) and then $CH_2Cl_2$/MeOH/AcOH (80:20:0.5). The fractions containing dye 340 were combined and concentrated to a solid.

Alternatively, fluorescein dyes 340 were synthesized from reactions of benzaldehyde derivatives 130 in dichlorobenzene with 10 equivalents of p-toluene sulfonic acid and the reaction mixture was heated with stirring at 130° C. for 3 hours.

6.5 Example 4

Extended fluorescein dyes of structure 440 were synthesized in reactions of 1,6-dihydroxy napthalene derivatives 320 and benzaldehyde derivatives as outlined in FIG. 4.

Following the alternative general dye synthesis conditions described for 340, 1,6-dihydroxynathalene 420 and benzaldehyde derivatives 130 were suspended in dichlorobenezene with 10 equivalents of p-toluene sulfonic acid and the reaction mixture was heated with stirring at 130° C. for 3 hours.

Following this general procedure, dye 19 below was produced from reactions of 1,6-dihydroxynapthalene 420 with compounds 130 where R11-R15=fluorine.

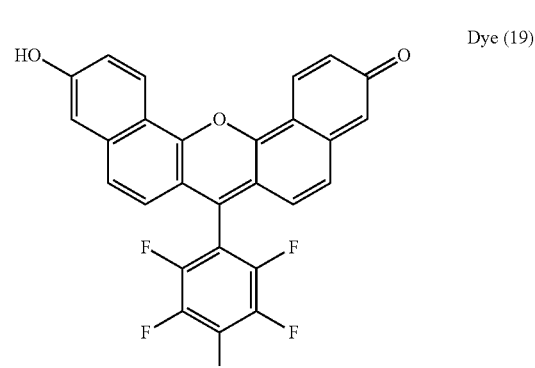

6.6 Example 5

Rhodol dyes of general structure 540 were synthesized from reactions of equal equivalents aminohydroxy benzene derivatives 120 or aminonapthol derivatives 220, dihydroxy benzene derivatives 320 or dihydroxynapthalene derivatives 420, and phenyl aldehydes 130, following the general procedure described for synthesis of 140 outlined in FIG. 5.

We claim:
1. A lipid soluble fluorescent phenyl xanthene dye having a structure of formula I:

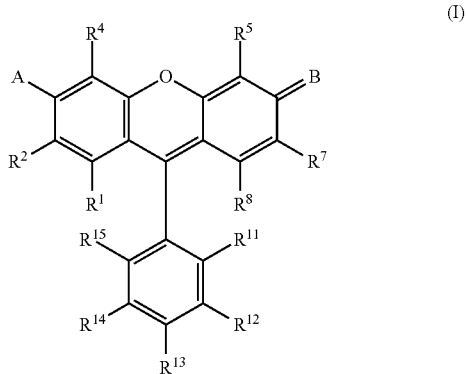

where A is —OH or NR3'R3";
B is =O or =N+R6'R6";
R1 is selected from hydrogen, Rx, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or alternatively, R1 may be taken together with R2 to form part of a benzo, naptho or polycyclic aryleno group which is optionally substituted with one or more of the same or different Ra or suitable Rb groups;

R2 is selected from hydrogen, Rx, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or alternatively, R2 may be taken together with R1 to form part of a benzo, naptho or polycyclic aryleno group which is optionally substituted with one or more of the same or different Ra or suitable Rb groups;

R3', when present, is selected from hydrogen, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups;

R3", when present, is selected from (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or, alternatively, R3" may be taken together with R4 to form a 5- or 6-membered ring which is optionally substituted with one or more of the same or different Ra or suitable Rb groups;

R4 is selected from hydrogen, Rx, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or, alternatively, when A is —NR3'R3", R4 may be taken together with R3" to form a 5- or 6-membered ring which is optionally substituted with one or more of the same or different Ra or suitable Rb groups;

R5 is selected from hydrogen, Rx, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or, alternatively, when B is —NR6'R6"+, R5 may be taken together with R6" to form a 5- or 6-membered ring which is optionally substituted with one or more of the same or different Ra or suitable Rb groups;

R6", when present, is selected from (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or, alternatively R6" may be taken together with R5 to form a 5- or 6-membered ring which is optionally substituted with one or more of the same or different Ra or suitable Rb groups;

R6', when present, is selected from hydrogen, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups;

R7 is selected from hydrogen, Rx, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or, alternatively, R7 may be taken together with R8 to form part of a benzo, naptho or polycyclic aryleno group which is optionally substituted with one or more of the same or different Ra or suitable Rb groups, or alternatively, when B is —NR6'R6"+, R7 may be taken together with R6' to form a 5- or 6-membered ring optionally substituted with one or more of the same or different Ra or suitable Rb groups;

R8 is selected from hydrogen, Rx, (C1-C20) alkyl or heteroalkyl optionally substituted with one or more of the same or different Rb groups, (C5-C20) aryl or heteroaryl optionally substituted with one or more of the same or different Ra or suitable Rb groups and (C6-C40) arylalkyl or heteroaryl alkyl optionally substituted with one or more of the same or different Ra or suitable Rb groups, or, alternatively, R8 together with R7 may form part of a benzo, naptho or polycyclic aryleno group which is optionally substituted with one or more of the same or different Ra or suitable Rb groups;

$R^{11}$ and/or $R^{15}$ are selected from alkyl, heteroalkyl, alkoxy, halo, haloalkyl, amino, alkylthio, cyano, isocyano, mercaptocyanato, nitro, and sulfinyl, and $R^{12}$, $R^{13}$, and $R^{14}$ are, independently, selected from hydrogen, alkyl, heteroalkyl, aryl, heteroaryl, alkoxy, halo, haloalkyl, amino, alkylthio, cyano, isocyano, cyanato, mercaptocyanato, nitro, sulfinyl, sulfonyl, sulfonamide, carboxyl, and carboxyamide;

$R^x$ is selected from —NR$^c$R$^c$, —OR$^d$, —SR$^d$, halo, haloalkyl, —CN, —NC, —OCN, —SCN, —NO, —NO$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$NR$^c$R$^c$, —C(O)R$^d$, —C(O)OR$^d$, —C(O)NR$^c$R$^c$, —C(NH)NR$^c$R$^c$, —OC(O)R$^d$, —OC(O)OR$^d$, —OC(O)NR$^c$R$^c$ and —OC(NH)NR$^c$R$^c$;

$R^a$ is selected from hydrogen, (C1-C8) alkyl or heteroalkyl, (C5-C20) aryl or heteroaryl and (C6-C28) arylalkyl or heteroarylalkyl;

$R^b$ is selected from —NR$^c$R$^c$, =O, —OR$^d$, =S, —SR$^d$, =NR$^d$, =NOR$^d$, halo, haloalkyl, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$NR$^c$R$^c$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —OC(O)R$^d$, —OC(O)OR$^d$, —OC(O)NR$^c$R$^c$ and —OC(NH)NR$^c$R$^c$;

each $R^c$ is independently hydrogen or $R^d$, or alternatively, each $R^c$ is taken together with the nitrogen atom to which it is bonded to form a 5- to 8-membered saturated or unsaturated ring which may optionally include one or more of the same or different additional heteroatoms and which may optionally be substituted with one or more of the same or different $R^a$ or $R^d$ groups;

each $R^d$ is independently $R^a$ or $R^a$ substituted with one or more of the same or different $R^a$ or $R^e$ groups;

each $R^e$ is selected from —$NR^aR^a$, =O, —$OR^a$, =S, —$SR^a$, =$NR^a$, =$NOR^a$, halo, haloalkyl, —CN, —NC, —OCN, —SCN, —NO, —$NO_2$, =$N_2$, —$N_3$, —$S(O)R^a$, —$S(O)_2R^a$, —$S(O)_2OR^a$, —$S(O)NR^aR^a$, —$S(O)_2NR^aR^a$, —$OS(O)R^a$, —$OS(O)_2R^a$, —$OS(O)_2NR^aR^a$, —$OS(O)_2OR^d$, —$OS(O)_2NR^aR^a$, —$C(O)R^a$, —$C(O)OR^a$, —$C(O)NR^aR^a$, —C(NH)$NR^cR^a$, —$OC(O)R^a$, —$OC(O)OR^a$, —$OC(O)NR^aR^a$ and —$OC(NH)NR^aR^a$; and wherein at least one of A, B, R1, R2, R4, R5, R7, R8, and R11-R15 has one or more lipophilic substituted groups selected from (C4-C20) alkyls, (C5-C40) aryls, and/or (C6-C40) arylalkyls.

2. The lipid soluble phenyl xanthene dye of claim 1 wherein the phenyl ring is only substituted with hydrogen, alkoxy, halo, and haloalkyl groups.

3. The lipid soluble phenyl xanthene dye of claim 1 wherein $R^{11}$ and $R^{15}$ are identical.

4. The lipid soluble phenyl xanthene dye of claim 1 wherein said dye is a fluorescein.

5. The lipid soluble phenyl xanthene dye of claim 1 wherein said dye contains one or more linkers that contain a linking group capable of forming a covalent or non-covalent linkage to a second substance.

6. The lipid soluble phenyl xanthene dye of claim 5 wherein said second substance is selected from a biomolecule, a glass substrate, a metal substrate and a polymer substrate.

7. The lipid soluble phenyl xanthene dye of claim 5 wherein said second substance is another dye and the phenyl xanthene dye is part of an energy transfer network.

8. A fluorescent phenyl xanthene dye comprising the following core structure:

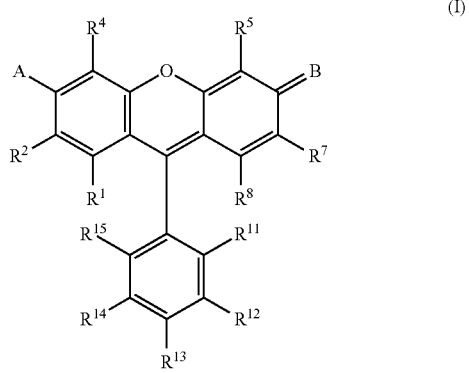

(I)

where A is —OH or $NR^{3'}R^{3''}$,
where B is a =O or =$N^+R^{6'}R^{6''}$;
where at least one of $R^{11}$ and $R^{15}$ is selected from alkyl, heteroalkyl, alkoxy, halo, haloalkyl, amino, alkylthio, cyano, isocyano, cyanato, mercaptocyanato, nitro, and sulfinyl, where one or more of $R^2$, $R^{3'}$, $R^{3''}$, $R^4$, $R^5$, $R^{6'}$, $R^{6''}$, $R^7$, $R^{12}$, $R^{13}$, and $R^{14}$ are optionally —S-LG or $S^1$-LK-$S^2$—CS, where S is a direct bond or a spacing moiety, LG is a linking group, $S^1$ and $S^2$ are, independently, a direct bond or a spacing moiety, LK is a linkage formed from a reacted linking group, and CS is a conjugated substance;

and the remainder of $R^1$, $R^2$, $R^{3'}$, $R^{3''}$, $R^4$, $R^5$, $R^{6'}$, $R^{6''}$, $R^7$, $R^8$, $R^{12}$, $R^{13}$, and $R^{14}$ are, independently, selected from hydrogen and a substituent having less than 40 atoms;

wherein at least one of A, B, R1, R2, R4, R5, R7, R8, and R11-R15 has one or more lipophilic substituted groups selected from (C4-C20) alkyls, (C5-C40) aryls, and/or (C6-C40) arylalkyls.

9. The phenyl xanthene dye of claim 8, wherein the substituents therein are further defined as follows:

$R^1$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or alternatively, $R^1$ may be taken together with $R^2$ to form part of a benzo, naptho or polycyclic aryleno group which is optionally substituted with one or more of the same or different $R^a$ or suitable $R^b$ groups;

$R^2$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or alternatively, $R^2$ may be taken together with $R^1$, to form part of a benzo, naptho or polycyclic aryleno group which is optionally substituted with one or more of the same or different $R^a$ or suitable $R^b$ groups, or alternatively, when A is —$NR^{3'}R^{3''}$, $R^2$ may be taken together with $R^{3'}$ to form a 5- or 6-membered ring which is optionally substituted with one or more of the same or different $R^a$ or suitable $R^b$ groups;

$R^{3'}$, when present, is selected from hydrogen, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^{3'}$ may be taken together with $R^2$ to form a 5- or 6-membered ring which is optionally substituted with one or more of the same or different $R^a$ or suitable $R^b$ groups;

$R^{3''}$, when present, is selected from (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^{3'}$ may be taken together with $R^4$ to form a 5- or 6-membered ring which is optionally substituted with one or more of the same or different $R^a$ or suitable $R^b$ groups;

$R^4$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, when B is —NR$^3$'R$^{3''}$R$^4$ may be taken together with R$^{3''}$ to form a 5- or 6-membered ring which is optionally substituted with one or more of the same or different $R^a$ or suitable $R^b$ groups;

$R^5$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, when B is —NR$^6$'R$^{6''}$+, R$^5$ may be taken together with R6' to form a 5- or 6-membered ring which is optionally substituted with one or more of the same or different $R^a$ or suitable $R^b$ groups;

$R^6$, when present, is selected from (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively R6'' may be taken together with R$^5$ to form a 5- or 6-membered ring which is optionally substituted with one or more of the same or different $R^a$ or suitable $R^b$ groups;

$R^{6'}$, when present, is selected from hydrogen, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^{6'}$ may be taken together with R$^7$ to form a 5- or 6-membered ring optionally substituted with one or more of the same or different $R^a$ or suitable $R^b$ groups;

$R^7$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^7$ may be taken together with R$^8$ to form part of a benzo, naptho or polycyclic aryleno group which is optionally substituted with one or more of the same or different $R^a$ or suitable $R^b$ groups, or, alternatively, when B is —NR$^6$'R$^{6''}$+, R$^7$ may be taken together with R6' to form a 5- or 6-membered ring optionally substituted with one or more of the same or different $R^a$ or suitable $R^b$ groups;

$R^8$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^8$ together with R$^7$ may form part of a benzo, naptho or polycyclic aryleno group which is optionally substituted with one or more of the same or different $R^a$ or suitable $R^b$ groups;

$R^{11}$ and $R^{15}$ are each, independently of one another, selected from halo, (C1-C20) alkyl, haloalkyl, —OR$^y$, —SR$^y$, —SOR$^y$, —SO$_2$R$^y$, and nitrile;

$R^{12}$, $R^{13}$ and $R^{14}$ are each, independently of one another, selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups;

$R^x$ is selected from —NR$^c$R$^c$, —OR$^d$, —SR$^d$, halo, haloalkyl, —CN, —NC, —OCN, —SCN, —NO, —NO$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$NR$^c$R$^c$, —C(O)R$^d$, —C(O)OR$^d$, —C(O)NR$^c$R$^c$, —C(NH)NR$^c$R$^c$, —OC(O)R$^d$, —OC(O)OR$^d$, —OC(O)NR$^c$R$^c$ and —OC(NH)NR$^c$R$^c$;

$R^y$ is selected from (C1-C20) alkyls or heteroalkyls optionally substituted with lipophilic substituents, (C5-C20) aryls or heteroaryls optionally substituted with lipophilic substituents and (C2-C26) arylalkyl or heteroarylalkyls optionally substituted with lipophilic substituents;

$R^a$ is selected from hydrogen, (C1-C8) alkyl or heteroalkyl, (C5-C20) aryl or heteroaryl and (C6-C28) arylalkyl or heteroarylalkyl;

$R^b$ is selected from —NR$^c$R$^c$, =O, —OR$^d$, =S, —SR$^d$, =NR$^d$, =NOR$^d$, halo, haloalkyl, —CN, —NC, —OCN, —SCN, —NO, —NO$_2$, =N2, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$NR$^c$R$^c$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —OC(O)R$^d$, —OC(O)OR$^d$, —OC(O)NR$^c$R$^c$ and —OC(NH)NR$^c$R$^c$;

each $R^c$ is independently hydrogen or $R^d$, or alternatively, each $R^c$ is taken together with the nitrogen atom to which it is bonded to form a 5- to 8-membered saturated or unsaturated ring which may optionally include one or more of the same or different additional heteroatoms and which may optionally be substituted with one or more of the same or different $R^a$ or $R^d$ groups;

each $R^d$ is independently $R^a$ or $R^a$ substituted with one or more of the same or different $R^a$ or $R^e$ groups; and each $R^e$ is selected from —NR$^a$R$^a$, =O, —OR$^a$, =S, —SR$^a$, =NR$^a$, =NOR$^a$, halo, haloalkyl, —CN, —NC, —OCN, —SCN, —NO, —NO$_2$, =N$_2$, —N$_3$, —S(O)R$^a$, —S(O)$_2$R$^a$, —S(O)$_2$OR$^a$, —S(O)NR$^a$R$^a$, —S(O)$_2$NR$^a$R$^a$, —OS(O)R$^a$, —OS(O)$_2$R$^a$, —OS(O)$_2$NR$^a$R$^a$, —OS(O)$_2$OR$^d$, —OS(O)$_2$NR$^a$R$^a$, —C(O)R$^a$, —C(O)OR$^a$, —C(O)NR$^a$R$^a$, —C(NH)NR$^a$R$^a$, —OC(O)R$^a$, —OC(O)OR$^a$, —OC(O)NR$^a$R$^a$ and —OC(NH)NR$^a$R$^a$ or, alternatively, one or more of $R^2$, $R^{3'}$, $R^{3''}$, $R^4$, $R^5$, $R^{6'}$, $R^{6''}$, $R^7$, $R^{12}$, $R^{13}$ and $R^{14}$ are each, independently of one another, selected from the group consisting of —S-LG and —S$^1$-LK-S$^2$—CS, wherein each S, which may be the same or different, is a direct bond or linker;

each LG, which may be the same or different, is a linking group;

each $S^1$ and $S^2$, independently, is a direct bond or linker;

each LK is a linkage formed from a reacted linking group; and each CS, which may be the same or different, is a conjugated substance.

10. The phenyl xanthene dye of claim 8 wherein -LG is an electrophilic group selected from activated esters, acrylamides, acyl azides, acyl halides, acyl nitriles, aldehydes, ketones, alkyl halides, alkyl sulfonates, anhydrides, aryl halides, aziridines, boronates, carboxylic acids, carbodiimides, diazoalkenes, epoxides, haloacetamides, halotriazines, imido esters, isocyanates, isothiocyanates, maleimides, phosphoramidites, silyl halides, sulfonate esters, and sulfonyl halides.

11. The phenyl xanthene dye of claim 8 wherein -LG is a nucleophilic group selected from amines, anilines, alcohols, phenols, thiols, hydrazines, and hydroxylamines.

12. The phenyl xanthene dye of claim 8 wherein —CS is a polymer, glass substrate, metal substrate, biomolecule or second dye.

13. The phenyl xanthene dye of claim 12 wherein the biomolecule is selected from peptides, polypeptides, proteins, amino acids, enzymes, receptors, antibodies, hormones, polysaccharides, carbohydrates, oligonucleotides, polynucleotides, nucleosides, and nucleic acids.

14. The phenyl xanthene dye of claim 12 wherein the second dye is selected from phenyl xanthene dyes, cyanine dyes, phthalocyanine dyes, squarine dyes, acridine dyes, alizarene dyes, azo dyes, anthraquinine dyes, BODIPY® dyes, coumarin dyes, lanthanide complexes, oxazine dyes, phenazathionium dyes, phenazoxonium dyes, porphyrin dyes, pyrene dyes, pyrilium dyes, perylene dyes, pheoxazine dyes and phenezine dyes.

* * * * *